(12) United States Patent
Nakamura et al.

(10) Patent No.: US 9,101,686 B2
(45) Date of Patent: Aug. 11, 2015

(54) CELL SUPPORT AND BONE REGENERATION MATERIAL

(75) Inventors: Kentaro Nakamura, Ashigarakami-gun (JP); Masaki Nakamura, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 13/582,396

(22) PCT Filed: Mar. 1, 2011

(86) PCT No.: PCT/JP2011/054618
§ 371 (c)(1),
(2), (4) Date: Aug. 31, 2012

(87) PCT Pub. No.: WO2011/108537
PCT Pub. Date: Sep. 9, 2011

(65) Prior Publication Data
US 2013/0004549 A1    Jan. 3, 2013

(30) Foreign Application Priority Data

Mar. 2, 2010 (JP) ................................ 2010-045050
Oct. 4, 2010 (JP) ................................ 2010-224627

(51) Int. Cl.
| | |
|---|---|
| *A61F 2/28* | (2006.01) |
| *C12P 21/06* | (2006.01) |
| *A61L 27/22* | (2006.01) |
| *A61L 27/18* | (2006.01) |
| *A61L 27/20* | (2006.01) |
| *A61L 27/38* | (2006.01) |
| *A61L 27/56* | (2006.01) |
| *A61L 27/58* | (2006.01) |

(52) U.S. Cl.
CPC ............... *A61L 27/222* (2013.01); *A61L 27/18* (2013.01); *A61L 27/20* (2013.01); *A61L 27/38* (2013.01); *A61L 27/56* (2013.01); *A61L 27/58* (2013.01)

(58) Field of Classification Search
None
See application file for complete search history.

(56) References Cited

U.S. PATENT DOCUMENTS

| | | |
|---|---|---|
| 5,266,476 A | 11/1993 | Sussman et al. |
| 5,830,493 A | 11/1998 | Yokota et al. |
| 6,051,425 A | 4/2000 | Morota et al. |
| 6,300,128 B1 | 10/2001 | Morota et al. |
| 2004/0063206 A1 | 4/2004 | Rowley et al. |
| 2005/0004242 A1 | 1/2005 | Sotome et al. |
| 2007/0166343 A1 | 7/2007 | Goerne et al. |
| 2010/0119574 A1 | 5/2010 | De Boer et al. |

FOREIGN PATENT DOCUMENTS

| | | |
|---|---|---|
| CN | 1158573 A | 9/1997 |
| JP | 62-122586 A | 6/1987 |
| JP | 08-089239 A | 4/1996 |
| JP | 2005-213449 A | 8/2005 |
| JP | 2007-143926 A | 6/2007 |
| JP | 2007-527435 A | 9/2007 |
| WO | 96/10426 A1 | 4/1996 |
| WO | 03/092759 A1 | 11/2003 |
| WO | 2008/103041 A1 | 8/2008 |
| WO | 2008133196 A1 | 11/2008 |
| WO | 2010/030714 A2 | 3/2010 |

OTHER PUBLICATIONS

Ko, In Kap, et al., "In vivo MR Imaging of Tissue-engineered Human Mesenchymal Stem Cells Transplated to Mouse: a Preliminary Study," Annals of Biomedical Engineering, Jan. 2007, pp. 101-108, vol. 35, No. 1.

Yamamoto, Masaya, et al., "Enhanced Osteoinduction by Biodegradable Gelatin B-tricalcium Phosphate Sponge Capable for Bone Morphogenetic Protein Release," International symposium of Maxillofacial & Oral Regenerative Biology in Okayama, 2005, pp. 286-287.

Hirose, Motohiro, et al., "Regenerative medicine utilizing regenerative cultured bone formed form mesenchymal cells," The Tissue Engineering 2007, Jul. 2007, pp. 178-183.

Ishii, Tatsuro, et al., "Clinical Evaluation of Bullet-Shaped Atelocollagen Sponge (Teruplug) as Protective Material for Tooth Extraction Wounds," Dental Outlook, Mar. 2001, pp. 665-677, vol. 97, No. 3.

Tabata, Yaushiko, Ph.D., et al., "Skull bone regeneration in primates in response to basic fibroblast growth factor," Journal of Neurosurgery, Nov. 1999, pp. 851-856, vol. 91.

International Preliminary Report on Patentability dated Sep. 13, 2012 for International Application No. PCT/JP2011/054618.

English translation of the International Preliminary Report on Patentability dated Sep. 20, 2012 for International Application No. PCT/JP2011/054618.

(Continued)

*Primary Examiner* — Jeffrey T Palenik
(74) *Attorney, Agent, or Firm* — Sughrue Mion, PLLC

(57) ABSTRACT

An object of the present invention is to provide a three-dimensional cell support that is capable of uniformly distributing cells and retaining the cells in a state without nonuniformity and is made of a biodegradable material. The present invention provides a cell support consisting of a porous body made of a biodegradable material, the porous body having the following properties:

(a) a porosity from 81% to 99.99%, (b) an average pore size of 10 to 400 μm, (c) having a hole interconnecting pores, and (d) a water absorption rate from 1000% to 9900%.

20 Claims, 21 Drawing Sheets
(1 of 21 Drawing Sheet(s) Filed in Color)

(56) References Cited

OTHER PUBLICATIONS

Office Action issued in corresponding Chinese Patent Application No. 201180011861.4, dated Nov. 25, 2013.
Chinese Patent Office, Office Action issued in Chinese Patent Application No. 201180011861.4, dated Nov. 25, 2013.
Official Action, dated Jun. 24, 2014, issued in counterpart Japanese Patent Application No. 2012-503186.
Song et al., "Bioactive and degradable hybridized nanofibers of gelatin-siloxane for bone regeneration," 2007, vol. 84A, No. 4, pp. 875-884.
Second Office Action, dated Jul. 17, 2014, issued in counterpart Chinese Application No. 201180011861.4.
Extended European Search Report, dated Aug. 25, 2014, issued in counterpart European Patent Application No. 11750647.7-1455.

5%

10%

Figure 5   Photograph of a slice of a collagen sponge
Day 1
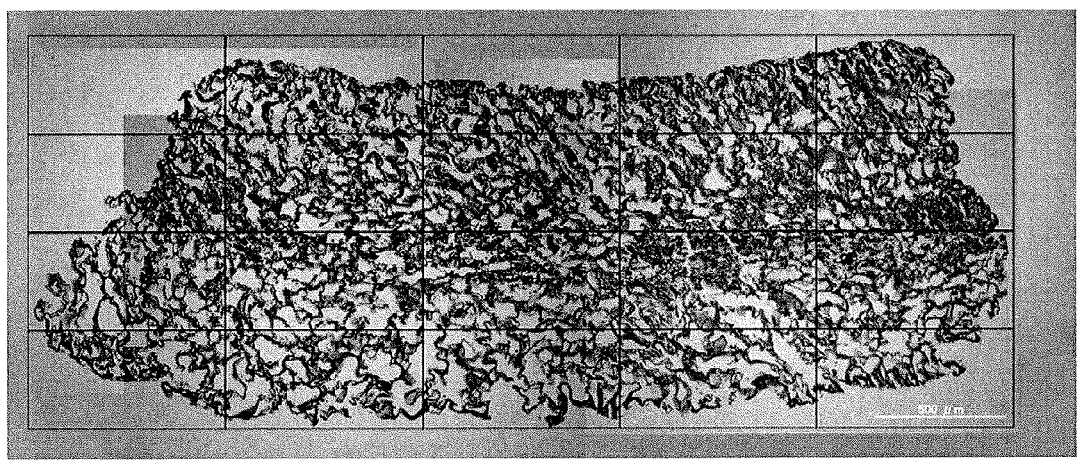
| number of cells per unit area ( /mm²) | | | | | Ave. | S.D. | CV |
|---|---|---|---|---|---|---|---|
| 637.6 | 1012.5 | 1091.1 | 1213.0 | 1220.1 | 1034.8 | 238.5 | 23% |
| 1651.0 | 1905.6 | 1487.2 | 2238.4 | 2953.1 | 2047.1 | 580.5 | 28% |
| 1605.9 | 2274.6 | 2344.6 | 2943.0 | 2999.3 | 2433.5 | 569.6 | 23% |
| 2863.9 | 1513.0 | 1242.0 | 1245.0 | 1285.6 | 1629.9 | 698.8 | 43% |
| | | | | | | | |
|---|---|---|---|---|---|---|---|
| Ave. | 1689.6 | 1676.4 | 1541.2 | 1909.8 | 2114.6 | 1786.3 | |
| S.D. | 911.8 | 540.9 | 559.9 | 837.3 | 995.5 | | 732.9 | |
| CV | 54% | 32% | 36% | 44% | 47% | | | 41% |

Figure 6  Photograph of a slice of the collagen sponge   Day 4
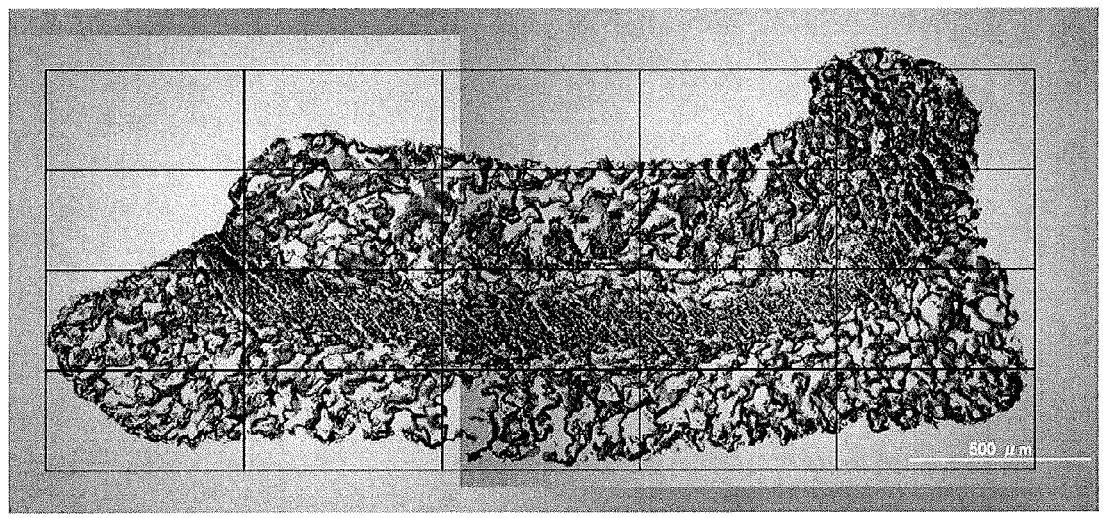
| number of cells per unit area ( /mm²) | | | | | Ave. | S. D. | CV |
|---|---|---|---|---|---|---|---|
| | 3502.8 | 3570.8 | 3653.1 | 3598.7 | 3581.3 | 62.5 | 2% |
| 6287.7 | 2659.5 | 2815.1 | 3375.1 | 6306.5 | 4288.8 | 1852.6 | 43% |
| 4452.3 | 7557.7 | 8015.5 | 7121.7 | 2662.5 | 5961.9 | 2306.2 | 39% |
| 3945.8 | 1377.4 | 1508.1 | 1093.5 | 1012.3 | 1787.4 | 1223.4 | 68% |
| Ave. | 4895.3 | 3774.3 | 3977.4 | 3810.8 | 3395.0 | 3921.9 | | |
| S. D. | 1232.2 | 2669.3 | 2823.7 | 2487.3 | 2216.0 | | 2182.3 | |
| CV | 25% | 71% | 71% | 65% | 65% | | | 56% |

Figure 7    hotograph of a slice of the recombinant gelatin sponge (10%) (diameter: 8 mm, height: 5 mm)   Day 1
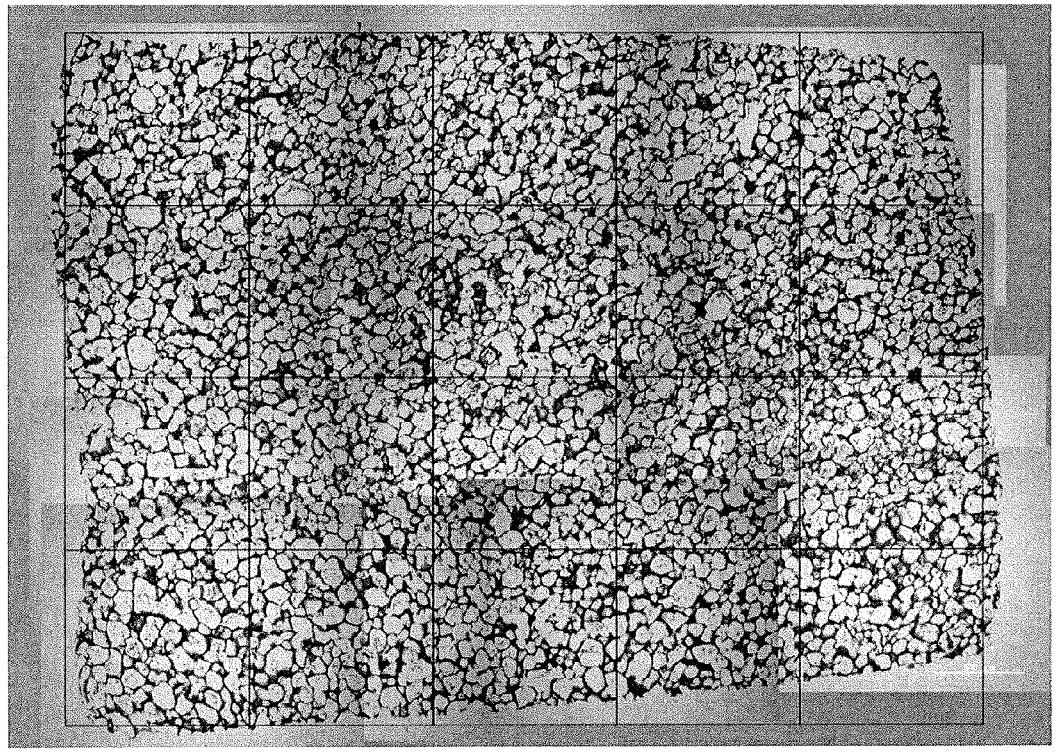
|  | number of cells per unit area ( /mm²) |  |  |  | Ave. | S. D. | CV |
|---|---|---|---|---|---|---|---|---|
|  | 316.4 | 423.4 | 543.2 | 474.9 | 658.3 | 483.3 | 128.2 | 27% |
|  | 525.3 | 386.8 | 434.2 | 553.9 | 591.8 | 498.4 | 85.3 | 17% |
|  | 434.3 | 415.4 | 441.8 | 610.9 | 584.2 | 497.3 | 92.5 | 19% |
|  | 585.0 | 315.7 | 254.4 | 218.1 | 271.1 | 328.9 | 147.4 | 45% |
| Ave. | 465.3 | 385.3 | 418.4 | 464.4 | 526.4 | 452.0 |  |  |
| S. D. | 117.0 | 49.0 | 120.1 | 173.4 | 173.4 |  | 129.3 |  |
| CV | 25% | 13% | 29% | 37% | 33% |  |  | 29% |

Figure 8  Photograph of a slice of the recombinant gelatin sponge (10%) (diameter: 8 mm, height: 5 mm)    Day 4
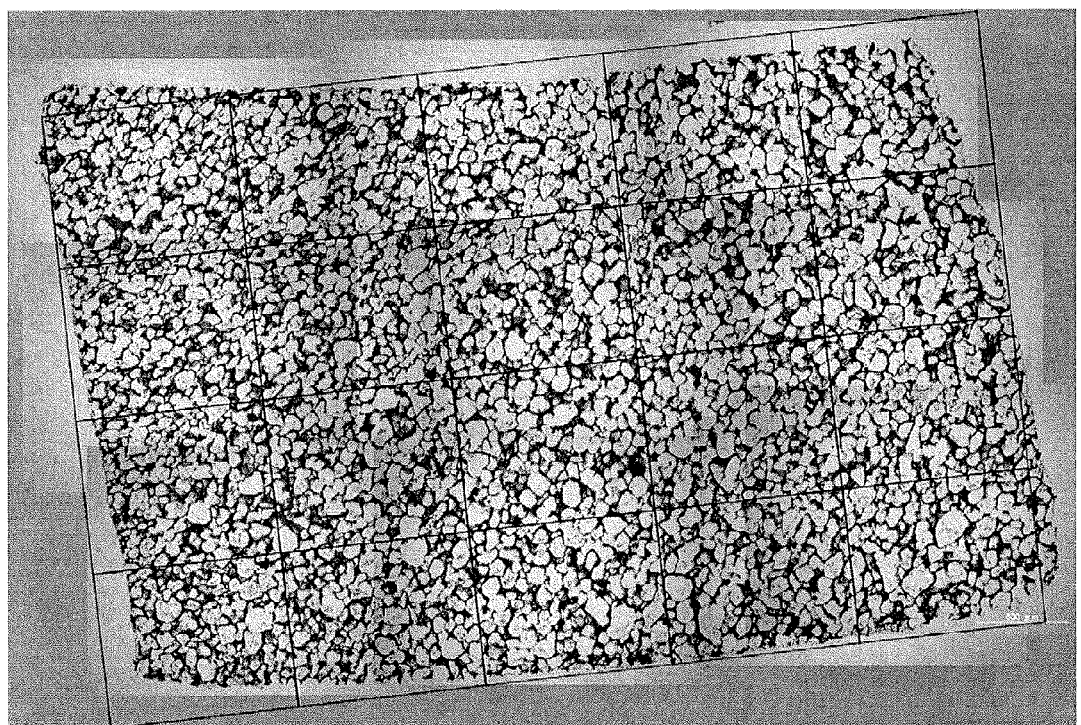
| | number of cells per unit area( /mm²) | | | | | Ave. | S.D. | CV |
|---|---|---|---|---|---|---|---|---|
| | 505.4 | 410.8 | 377.1 | 311.6 | 263.2 | 373.6 | 93.3 | 25% |
| | 383.9 | 313.4 | 357.1 | 454.6 | 390.7 | 379.9 | 51.6 | 14% |
| | 497.5 | 297.9 | 256.7 | 326.4 | 445.4 | 364.8 | 102.2 | 28% |
| | 795.8 | 382.5 | 379.2 | 324.7 | 444.2 | 465.3 | 189.5 | 41% |
| Ave. | 545.7 | 351.1 | 342.5 | 354.3 | 385.9 | 395.9 | | |
| S.D. | 175.8 | 54.1 | 58.1 | 67.2 | 85.7 | | 117.8 | |
| CV | 32% | 15% | 17% | 19% | 22% | | | 30% |

Figure 9 Photograph of a slice of an atelocollagen honeycomb sponge Day 1
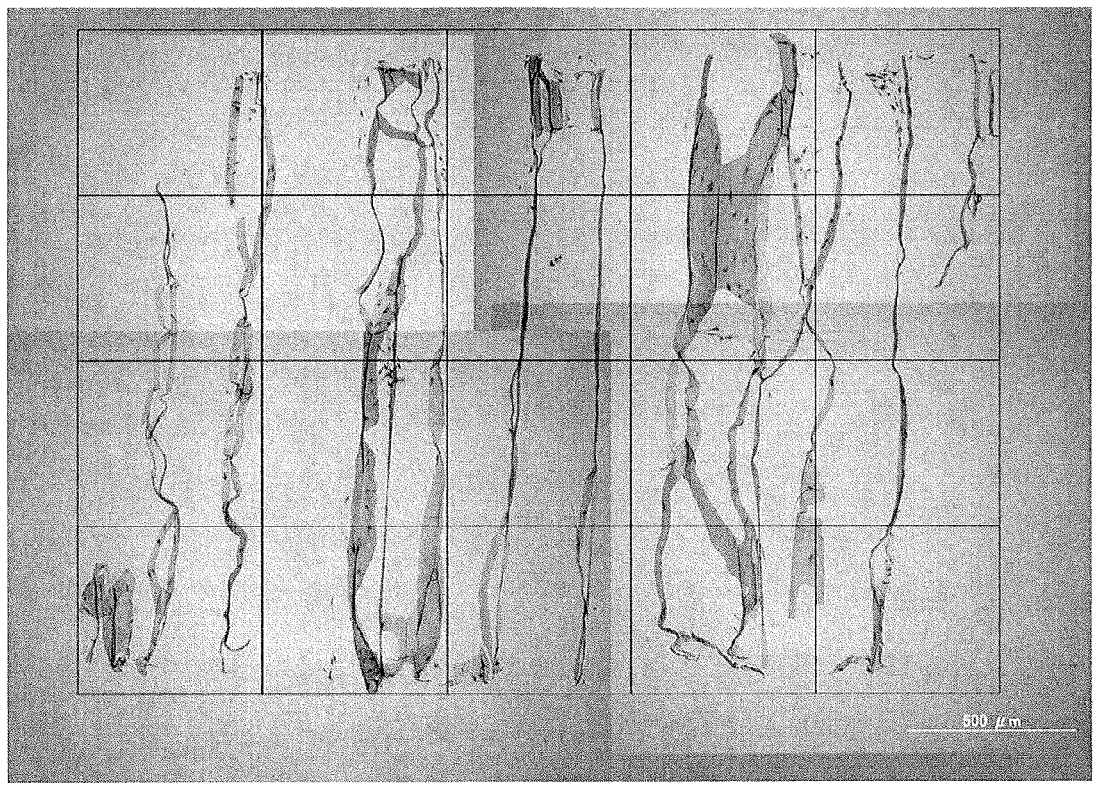
|   | number of cells per unit area( /mm²) | | | | | Ave. | S.D. | CV |
|---|---|---|---|---|---|---|---|---|
|   | 310.8 | 203.3 | 111.2 | 203.8 | 308.1 | 227.4 | 83.9 | 37% |
|   | 112.1 | 102.5 | 34.5 | 190.7 | 95.4 | 107.1 | 55.8 | 52% |
|   | 68.6 | 125.9 | 15.3 | 72.5 | 39.0 | 64.3 | 41.6 | 65% |
|   | 141.8 | 90.5 | 79.1 | 49.0 | 188.4 | 109.8 | 55.3 | 50% |
| Ave. | 158.3 | 130.6 | 60.0 | 129.0 | 157.7 | 127.1 | | |
| S.D. | 106.0 | 50.6 | 43.3 | 79.6 | 117.7 | | 83.8 | |
| CV | 67% | 39% | 72% | 62% | 75% | | | 66% |

Figure 10  Photograph of a slice of the atelocollagen honeycomb sponge   Day 4
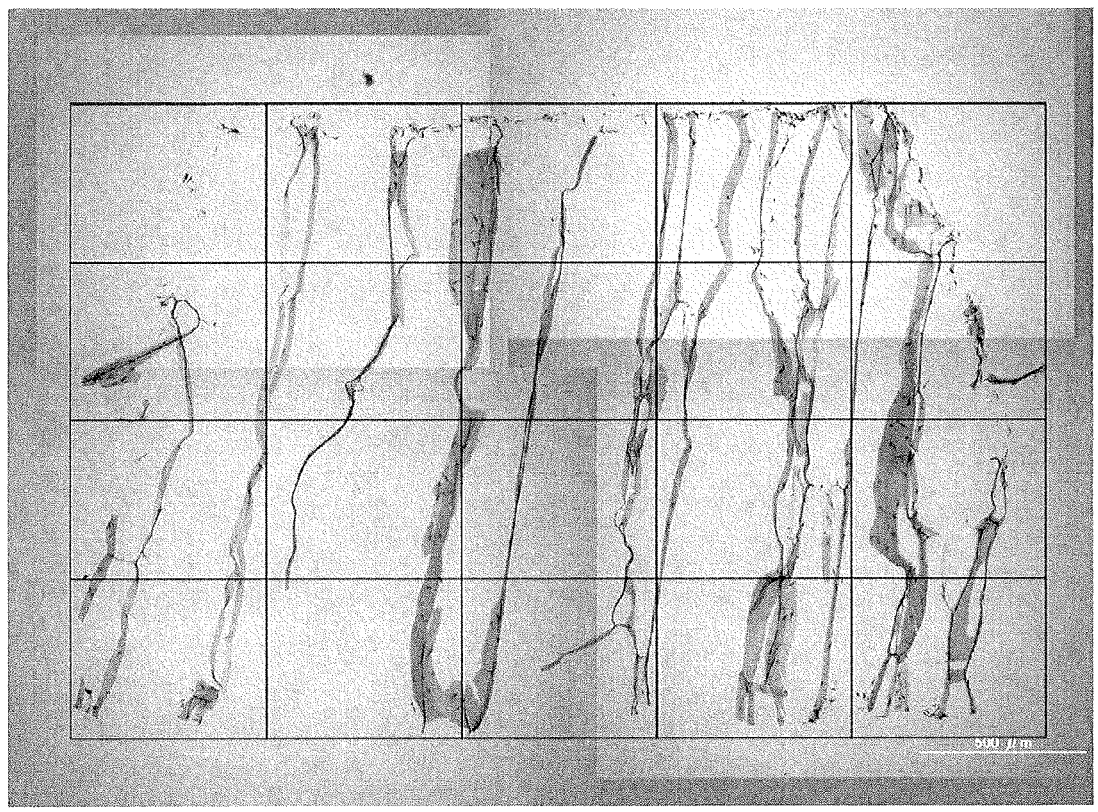
|  | number of cells per unit area ( /mm²) | | | | | Ave. | S.D. | CV |
|---|---|---|---|---|---|---|---|---|
|  | 205.1 | 152.8 | 179.9 | 328.6 | 404.4 | 254.2 | 107.6 | 42% |
|  | 151.2 | 25.4 | 32.4 | 101.6 | 177.3 | 97.6 | 68.4 | 70% |
|  | 56.4 | 32.7 | 7.3 | 86.3 | 190.8 | 74.7 | 71.2 | 95% |
|  | 103.2 | 41.2 | 39.7 | 128.6 | 242.8 | 111.1 | 83.2 | 75% |
| Ave. | 129.0 | 63.0 | 64.8 | 161.3 | 253.8 | 134.4 | | |
| S.D. | 63.8 | 60.2 | 77.9 | 112.9 | 104.3 | | 105.6 | |
| CV | 50% | 96% | 120% | 70% | 41% | | | 79% |

Figure 11  Photograph of a slice of the recombinant gelatin sponge (10%) (2 mm × 2 mm × 3 mm)   Day 1
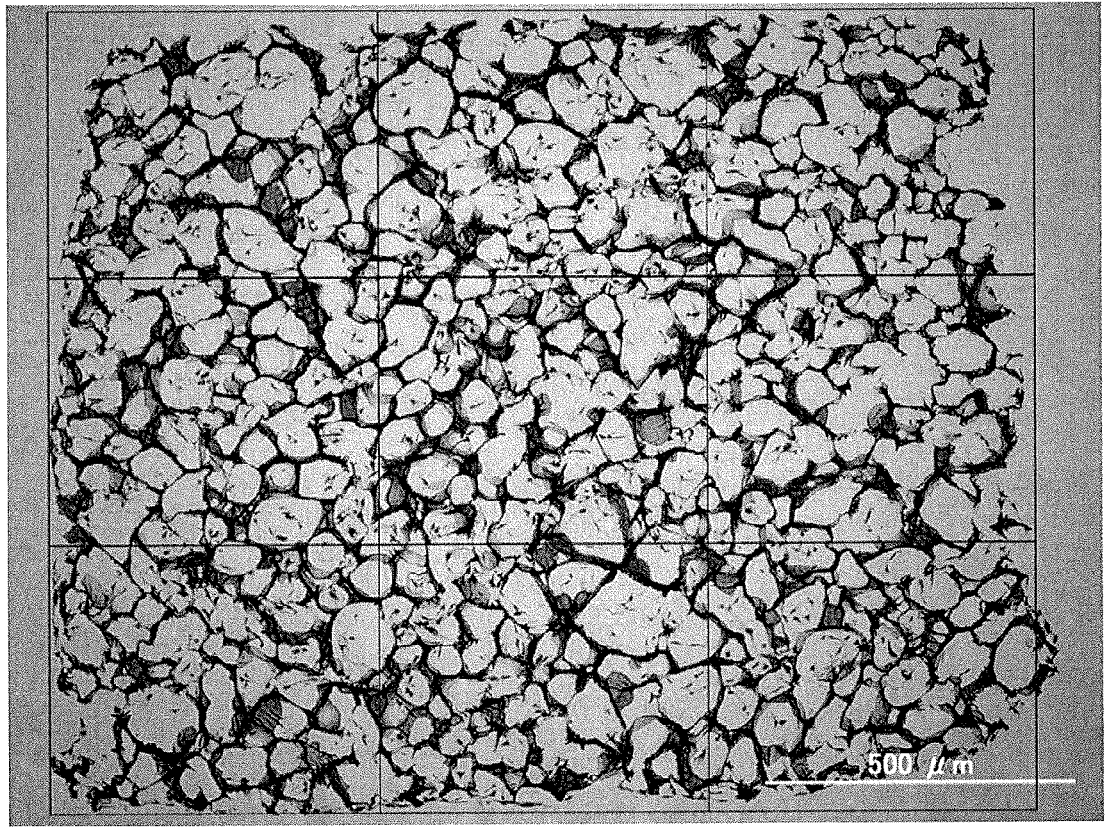
|      | number of cells per unit area ( /mm²) | | | Ave. | S.D. | CV |
|------|-------|-------|-------|-------|-------|-----|
|      | 490.2 | 700.7 | 388.6 | 526.5 | 159.2 | 30% |
|      | 517.7 | 435.3 | 250.0 | 401.0 | 137.1 | 34% |
|      | 483.4 | 616.2 | 464.5 | 521.4 | 82.7  | 16% |
| Ave. | 497.1 | 584.1 | 367.7 | 483.0 |       |     |
| S.D. | 18.2  | 135.6 | 108.7 |       | 128.6 |     |
| CV   | 4%    | 23%   | 30%   |       |       | 27% |

Figure 12   Photograph of a slice of the recombinant gelatin sponge (10%) (2 mm × 2 mm × 3 mm)   Day 4
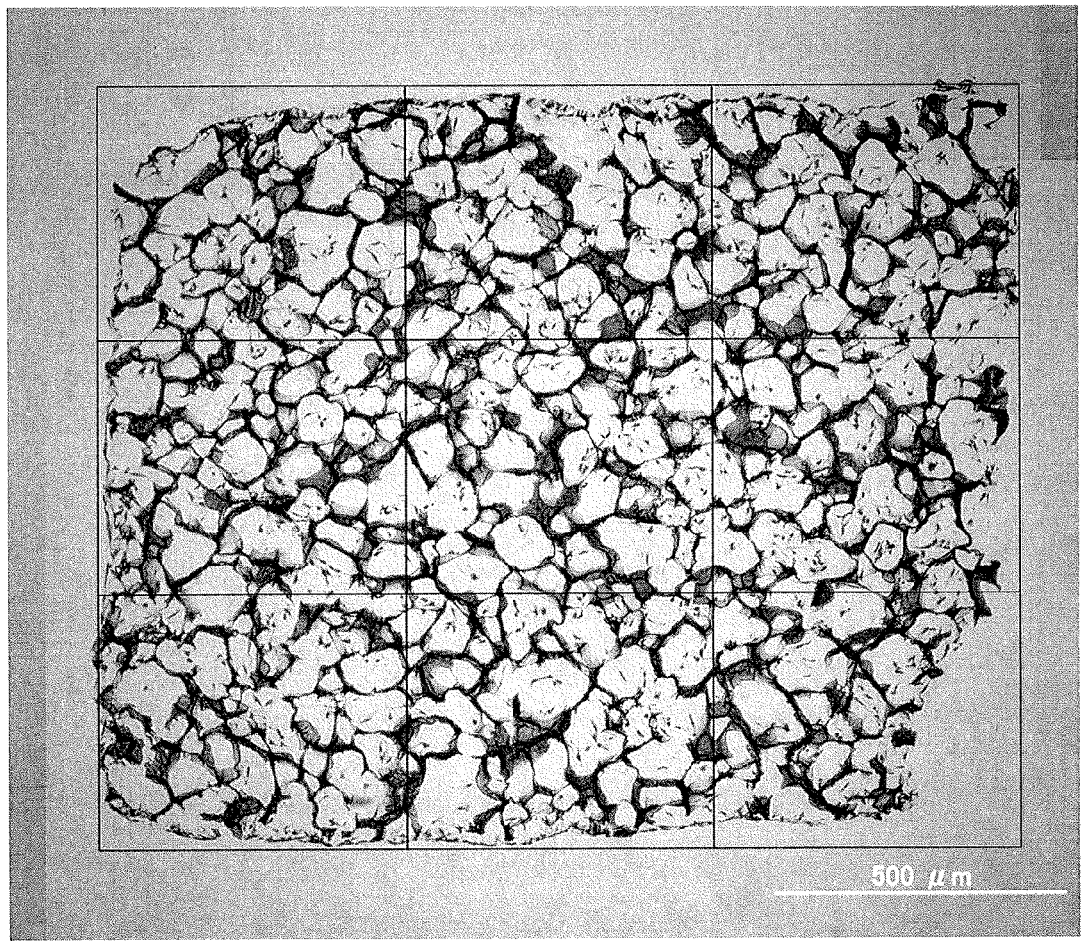
| | number of cells per unit area ( /mm²) | | | Ave. | S.D. | CV |
|---|---|---|---|---|---|---|
| | 544.3 | 643.7 | 614.5 | 600.8 | 51.1 | 9% |
| | 356.4 | 452.6 | 596.6 | 468.5 | 120.9 | 26% |
| | 465.7 | 563.7 | 656.0 | 561.8 | 95.2 | 17% |
| Ave. | 455.5 | 553.3 | 622.4 | 543.7 | | |
| S.D. | 94.4 | 96.0 | 30.5 | | 100.2 | |
| CV | 21% | 17% | 5% | | | 18% |

Figure 13   Photograph of a slice of collagen gel-embedding culture
Day 1
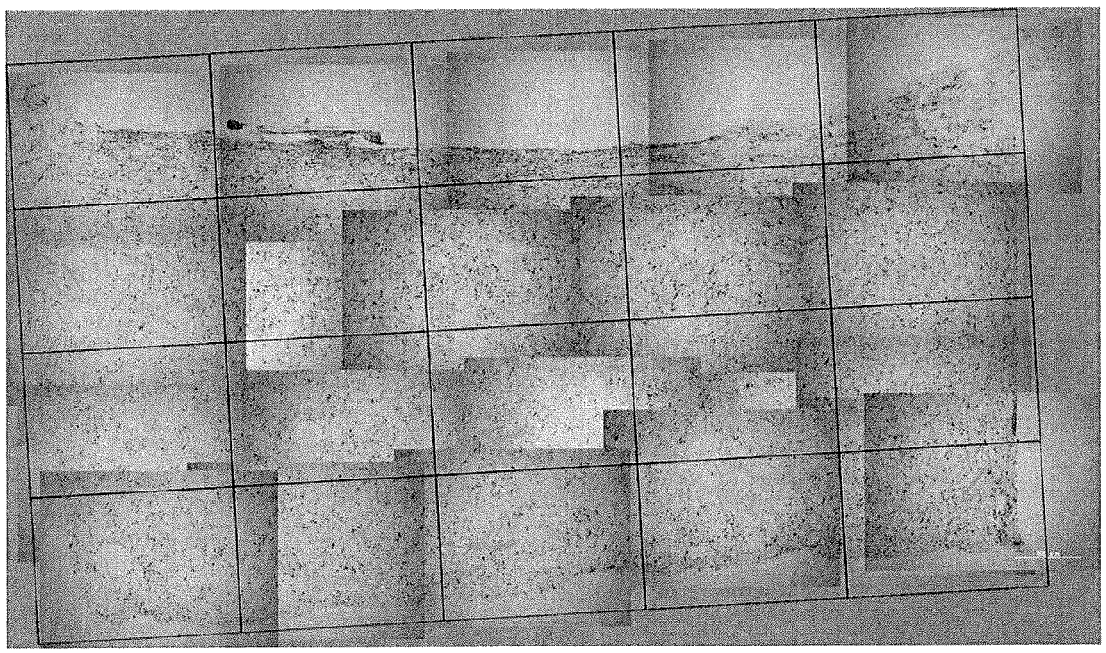
| | number of cells per unit area( /mm²) | | | | | Ave. | S.D. | CV |
|---|---|---|---|---|---|---|---|---|
| | 771.7 | 900.3 | 1045.0 | 523.8 | 336.5 | 715.4 | 285.6 | 40% |
| | 370.6 | 553.3 | 489.9 | 355.2 | 386.1 | 431.0 | 86.4 | 20% |
| | 327.0 | 306.3 | 288.2 | 243.7 | 381.9 | 309.4 | 50.8 | 16% |
| | 505.3 | 393.6 | 312.1 | 393.4 | 512.4 | 423.4 | 84.9 | 20% |
| Ave. | 493.6 | 538.4 | 533.8 | 379.0 | 404.2 | 469.8 | | |
| S.D. | 200.3 | 262.0 | 352.5 | 115.5 | 75.5 | | 210.8 | |
| CV | 41% | 49% | 66% | 30% | 19% | | | 45% |

Figure 14  Photograph of a slice of collagen gel-embedding culture
Day 4
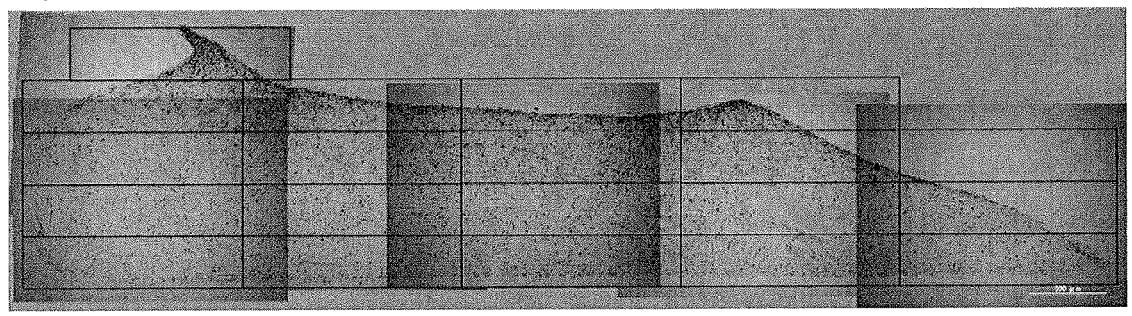
| number of cells per unit area ( /mm²) | | | | | Ave. | S.D. | CV |
|---|---|---|---|---|---|---|---|
| 2427.9 | | | | | 2427.9 | #DIV/0! | #DIV/0! |
| 972.9 | 1430.5 | 1998.6 | 2108.9 | | 1124.0 | 410.5 | 37% |
| 636.3 | 840.0 | 1227.0 | 1211.9 | 1704.8 | 707.0 | 130.2 | 18% |
| 528.7 | 640.5 | 723.1 | 770.3 | 872.2 | 707.0 | 130.2 | 18% |
| 510.7 | 624.0 | 894.5 | 890.3 | 836.1 | 751.1 | 174.0 | 23% |
| Ave. | 1015.3 | 883.8 | 1210.8 | 1245.4 | 1137.7 | 1092.5 | | |
| S.D. | 811.2 | 377.5 | 565.3 | 605.1 | 491.4 | | 560.1 | |
| CV | 80% | 43% | 47% | 49% | 43% | | | 51% |

Figure 15   photograph of a slice of culture on a collagen gel
Day 1
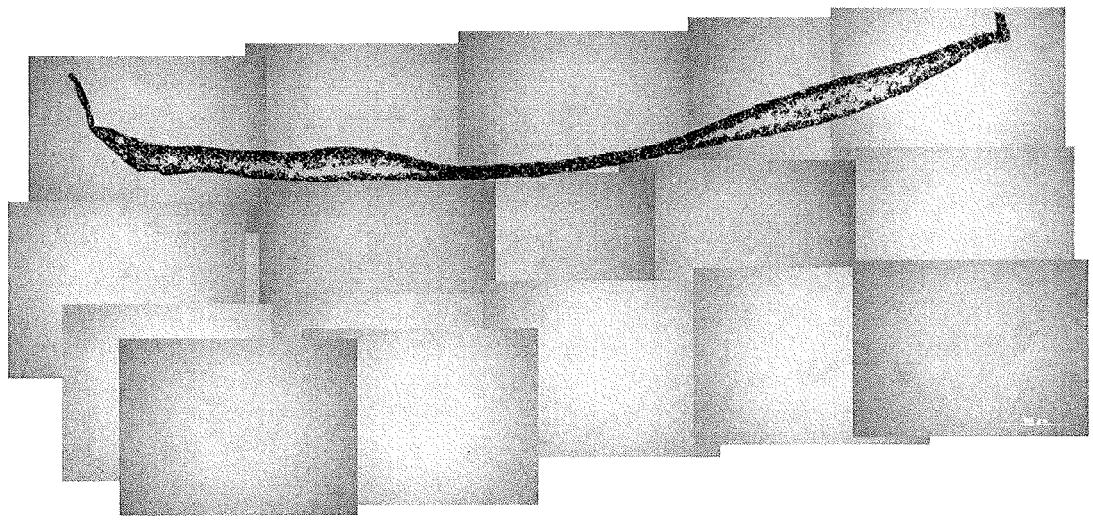
Figure 16   Photograph of a slice of culture on the collagen gel.
Day 4
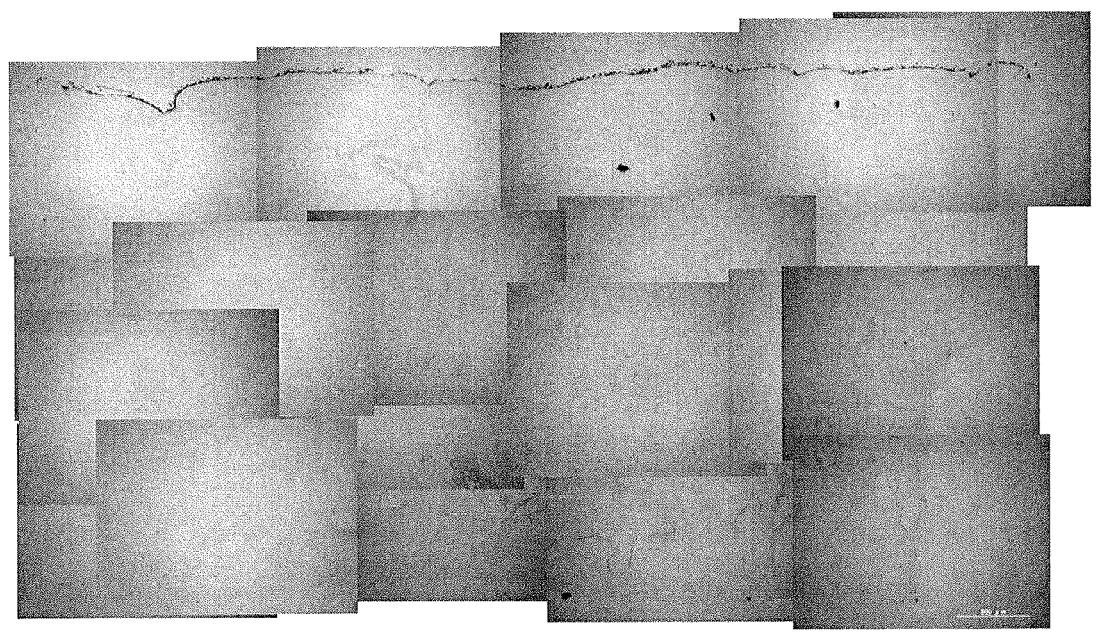

Figure 17   Results of a cell adhesiveness test (DNA assay)
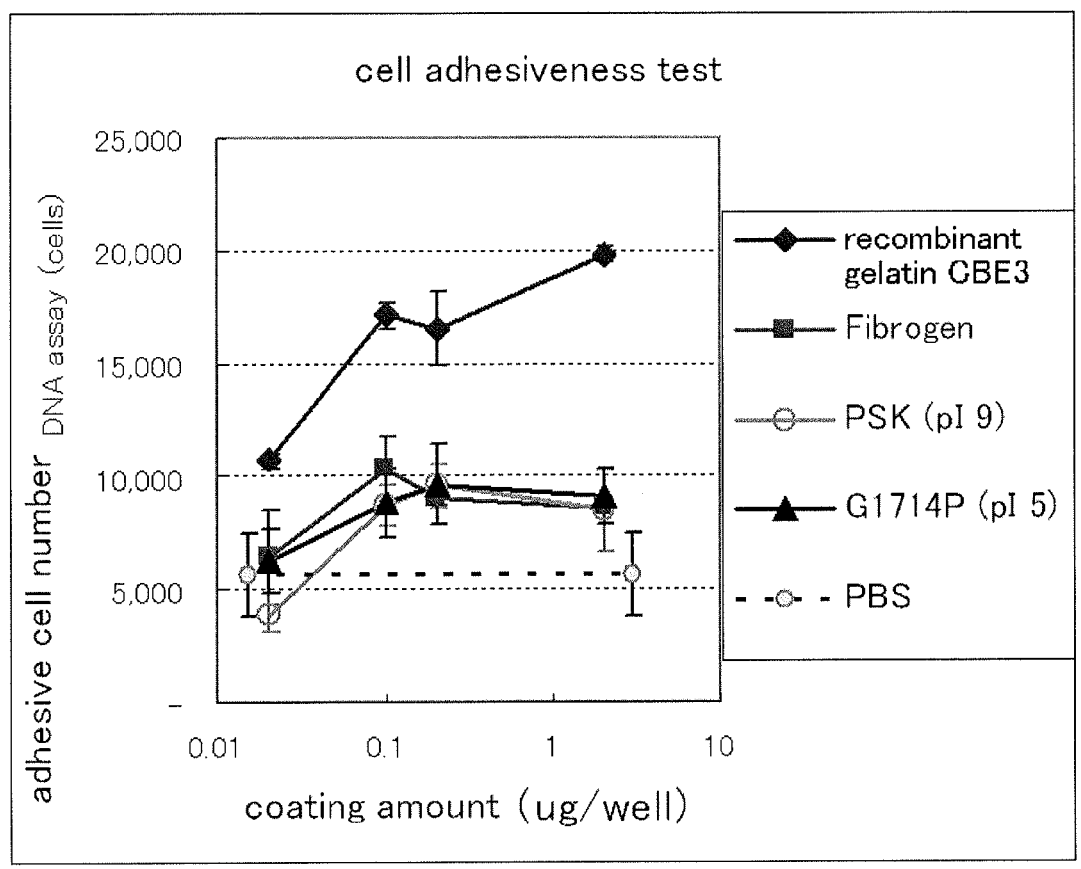

Figure 18 Results of a cell adhesiveness test (DNA assay).
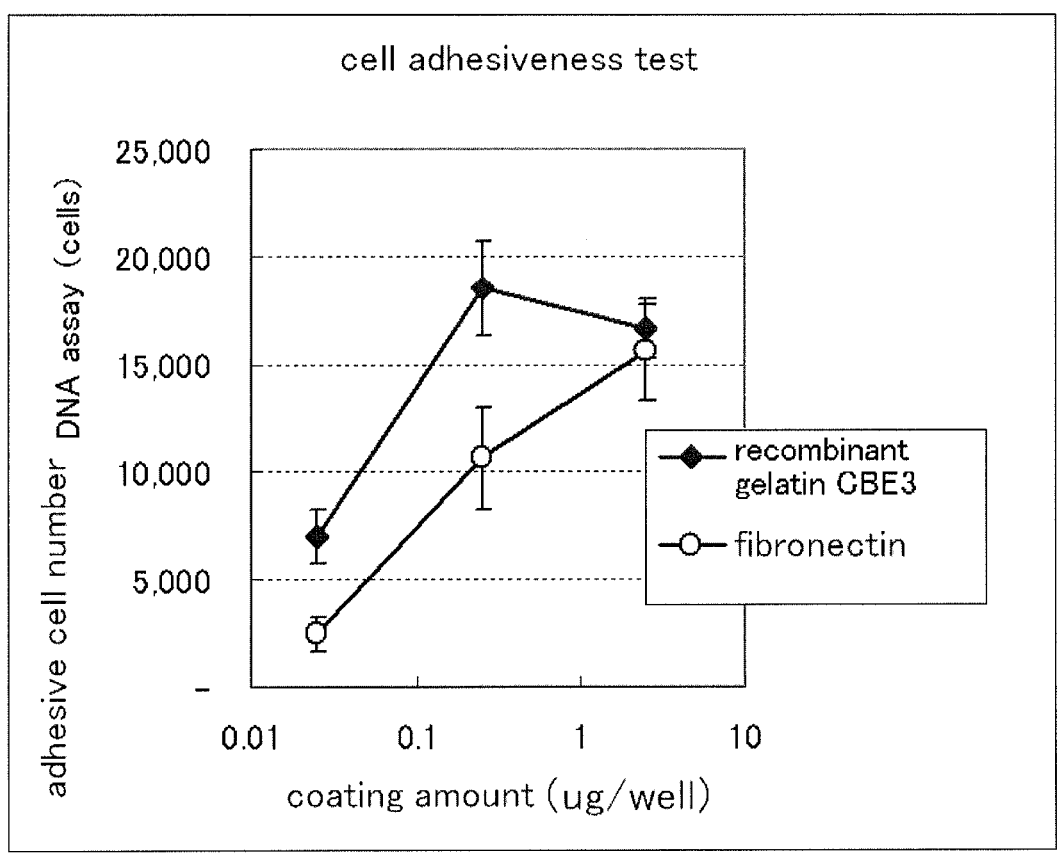

Figure 19  Manner of cell adhesion to a recombinant gelatin-coated plate
Photographs of HUVEC cells on various protein-coated plate
R-Gel: recombinant gelatin CBE3
Fibrogen: recombinant collagen of Fibrogen Inc.
G1917P: beef bone-derived gelatin
PSK: pork skin-derived gelatin
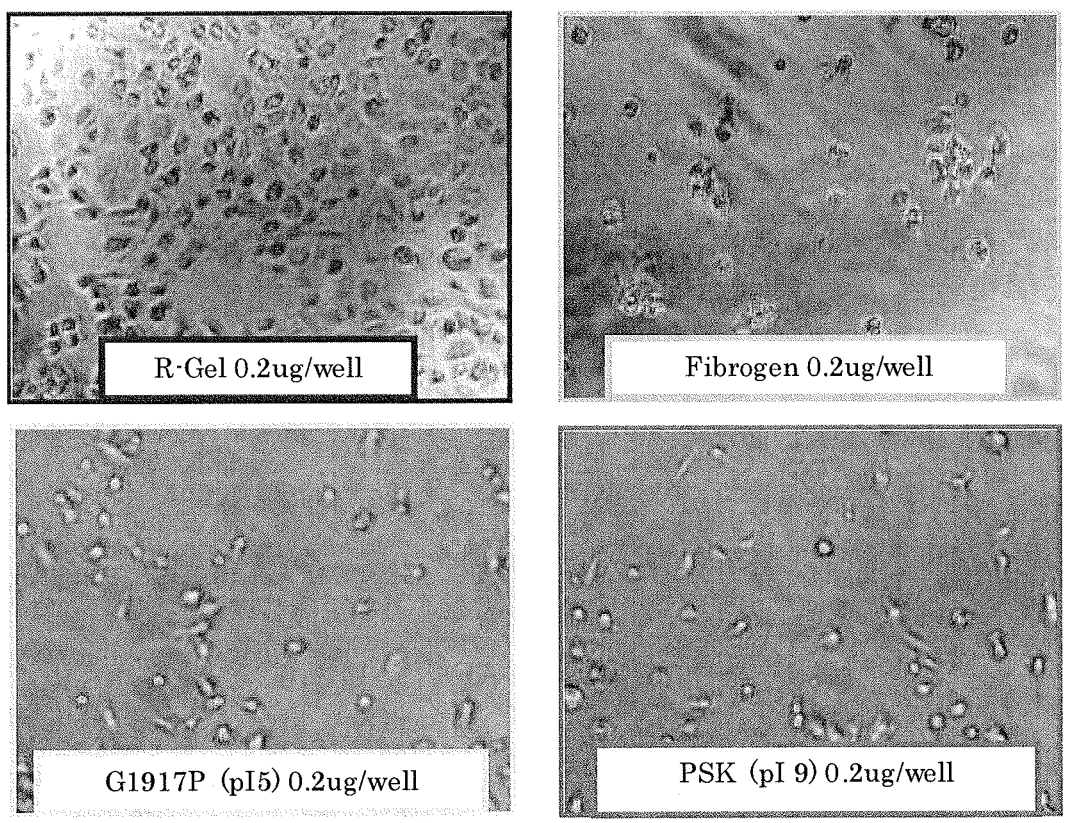

Rat cranial defect model.
Left: macroscopic photograph. Right: μCT photograph (Micro-CT image: Tissue Eng (2007) 13 (3): 501 - 12)

CELL SUPPORT AND BONE REGENERATION MATERIAL

CROSS REFERENCE TO RELATED APPLICATIONS

This application is a National Stage of International Application No. PCT/JP2011/054618 filed on Mar. 1, 2011, which claims priority from Japanese Patent Application Nos. 2010-045050, filed on Mar. 2, 2010 and JP 2010-224627, filed Oct. 4, 2010, the contents of all of which are incorporated herein by reference in their entirety.

TECHNICAL FIELD

The present invention relates to a cell support capable of uniformly distributing cells, and a bone regeneration material.

BACKGROUND ART

The practical utilization of regenerative medicine, which helps the regeneration of living tissues/organs that have fallen into functional disorder or functional incompetence, is currently proceeding. The regenerative medicine is novel medical technology of re-creating the same or similar forms or functions as in original tissues using 3 factors, i.e., cells, scaffolds, and growth factors, for living tissues that no longer recover by only natural healing ability possessed by organisms. In recent years, treatments using cells have been being gradually realized. Examples thereof include cultured epidermis using autologous cells, cartilage treatment using autologous cartilage cells, bone regeneration treatment using mesenchymal stem cells, cardiac muscle cell sheet treatment using myoblasts, corneal regeneration treatment using corneal epithelial sheets, and nerve regeneration treatment. These novel treatments, unlike conventional alternative medicine based on artificial materials (bone prosthetic materials or hyaluronic acid injection), help the repair or regeneration of living tissues and therefore produce high therapeutic effects. In fact, products such as cultured epidermis or cultured cartilage using autologous cells have been launched.

However, the problem of the variability of therapeutic effects or the problem of unexpected adverse effect has been in concern and has arisen actually in the treatments using cells as described above. Leading causes of such problems are considered to be the heterogeneity of cells obtained in culture and the nonuniform engraftment of cells at transplantation sites.

For example, it is known that cartilage cells tend to be dedifferentiated during the course of culture, and therefore, a culture method keeping them in a constant state has been demanded. Moreover, it is known that a cell generally changes its state depending on conditions under which the cell is present, particularly, cell density. For example, it is known that mesenchymal stem cells (MSCs), which are currently expected to be applied to treatments, tend to be differentiated into fat cells under low cell density conditions and, on the contrary, differentiated into osteocytes under high cell density conditions. For other cells as well, a very important factor is to control cell density at a constant level.

Meanwhile, many reports have demonstrated that a three-dimensional culture technique is important for efficiently culturing cells under conditions closer to an in vivo environment. However, it is known that when cells are inoculated to a three-dimensional matrix, the cells are not uniformly distributed in the matrix and are disproportionately located in the matrix. For the three-dimensional culture, it is therefore difficult to keep cell density constant. Although the three-dimensional cell culture presumably depends on the physical, biological and chemical properties of matrices, such as the adhesiveness of matrices to cells, the structure of matrices, and the hydrophilicity and hydrophobicity of matrices, it is generally difficult to uniformly distribute cells in a three-dimensional matrix and keep cell density constant. As a result, the state in which a cell state is not uniform in the three-dimensional matrix is formed, resulting in problems associated with cell homogeneity.

Moreover, for transplantation treatment using the obtained cells, the transplantation of cells cultured, for example, as in the atelocollagen gel-embedding culture of cartilage cells, together with a matrix is performed, in addition to the injection of a cell suspension. In this case, after culture, a construct consisting of a three-dimensional matrix and cells is trimmed appropriately for the shape of a transplantation site and transplanted thereto. If the cells are nonuniformly distributed in the three-dimensional matrix, nonuniform cell distribution also occurs in a fragment for transplantation obtained by trimming, generating a site strongly exhibiting therapeutic effects and a site hardly exhibiting therapeutic effects. Furthermore, the nonuniform cell density causes nonuniformity in the physical properties and physical strength of the transplanted fragment. Such nonuniformity becomes a factor responsible for the variability of therapeutic effects and reduction in the survival rate of the transplanted fragment and results in a lack of expected therapeutic effects. Furthermore, for aptitude required for the three-dimensional matrix as described above, it is important to be made of a material having biocompatibility, desirably biodegradability (because of the need for being spontaneously degraded in vivo), because of its use in transplantation. Unfortunately, there has not existed a three-dimensional matrix that satisfies all of these requirements.

As described above, from the viewpoint of regenerative medicine using cells, it is required that the three-dimensional matrix should be capable of uniformly distributing cells and retaining the cells in a state without nonuniformity both in a culture step and in a transplantation step and be also made of a biodegradable material because of the need for being applied to transplantation. Previous porous polymers, three-dimensional collagen matrices, or collagen gel-embedding culture have hardly overcome such a problem.

In general, living tissues are composed of cells and extracellular matrices (polymer constructs). Various life phenomena are consequences of their complicated interactions. Cells release various growth factors (drugs) and influence their own functions or the functions of other cells. On the other hand, the extracellular matrices secreted from the cells provide hydration space for cell functions, function as drug depots or scaffolds, and have significant influence on the functional manifestation or differentiation of cells.

The regenerative medicine, which has made remarkable progress in recent years, is gathering a lot of attention as highly advanced medicine that may substitute for artificial organs or organ transplantation. For realizing the regenerative medicine, it is important to wield each of principal factors in the regenerative medicine, i.e., cells, culture apparatuses, growth factors (drugs), and cell scaffolds (artificial extracellular matrices and materials).

Bone regeneration in the orthopedic or dental field is known as a region that is gathering a lot of attention in the regenerative medicine field. Bone diseases affecting legs or lower backs cause inability to walk, while bone diseases affecting teeth make dietary intake difficult. Thus, a bone disease causes remarkable reduction in QOL.

Infuse (combination of BMP-2 with a collagen sponge) treating spinal cord injury as well as BioOss (deproteinized bovine bone powder) and Gem21 (PDGF and βTCP) as bone prosthetic materials regenerating alveolar bone are known as current typical preparations for bone regeneration treatment. In general, [1] strength for structural maintenance, [2] securing of space for bone regeneration, [3] scaffolds for cells to regenerate bone, [4] induction of differentiation and growth of cells to regenerate bone, and [5] degradability associated with bone regeneration are known as properties required for preparations for bone regeneration treatment. Collagen, βTCP, or the like is widely used as a scaffold material for the preparations for bone regeneration treatment. Moreover, at the research level, bone regeneration has been performed by impregnating a gelatin (denatured form of collagen) sponge with bFGF or BMP-2 (Journal of Neurosurgery 91 851-856, 1999). Furthermore, studies have also been made on bone regeneration treatment using a therapeutic agent obtained by involving bone marrow mesenchymal stem cells in a scaffold matrix and culturing it (Motohiro Hirose and Hajime Ogushi, "Regenerative Medicine of Bone Using Regenerated Cultured Bone Tissues", The Tissue Engineering 2007, 178-183; 2007.7).

The bone regeneration means that osteoblasts generate bone matrices to form hard bone consisting of osteocytes and the bone matrices, and is a phenomenon achieved by the osteoblasts. Not only the utilization of a cell graft (bone marrow mesenchymal stem cells, etc.) grown ex vivo but also the bone regenerating effect of growth factors (drugs) induces bone regeneration by the action on host-derived cells in a neighborhood thereof. For example, BMP differentiates undifferentiated mesenchymal cells into osteoblasts by its action and activates bone formation by the osteoblasts. Thus, since cells predominate in the bone regeneration, a scaffold material serving as a cell scaffold is very highly important.

Gelatin is well known as a typical scaffold material in general regenerative medicine. Gelatin is known as a material having high biocompatibility and high safety and has a good record with medical applications. Likewise, collagen is known as a material having a good record, but is lower soluble than gelatin and is largely limited by the concentration and pH of its solution (collagen cannot be prepared into a solution with a high concentration of dozens of %, a neutral solution, or the like). Hence, there are usually limitations on products into which collagen may be processed, prepared, or molded. Thus, a scaffold matrix using gelatin is desirable. However, there is a general perception that the gelatin matrix is less suitable as a scaffold material particularly for bone regeneration treatment. For example, it is disclosed that a gelatin sponge alone inhibits bone regeneration (Tabata, et al., Journal of Neurosurgery 91 851-856, 1999). Moreover, Ishii et al. (Dental Outlook, 97 (3), 665-677, 2001) have examined the influence of a collagen sponge and a gelatin sponge on the ability to regenerate alveolar bone and stated that gelatin lacks the ability to regenerate bone, compared with collagen.

In addition, since the bone regenerating power of a scaffold material alone is insufficient in case of collagen, ceramic materials, or synthetic polymers, their combinations with BMP, autologous blood, or autologous bone marrow mesenchymal stem cells have been reported under the present circumstances.

A cause of the absence of the favorable ability of these scaffold materials to regenerate bone has been considered to be insufficient "ability to infiltrate (introduce) cells into the scaffold matrix" or insufficient "ability to distribute or retain cells in the scaffold matrix". The present inventors have thought that the absence of sufficient cell introducing power, distribution, or retaining power of the scaffold matrix as a cell support is responsible for not leading to bone regeneration.

For example, JP Patent Publication (Kokai) No. 62-122586 A (1987) discloses a porous support having a porosity of 40 to 95%, desirably 60 to 80% or lower, which consists of polyester or polypropylene. The porous support with the porosity cannot uniformly distribute or retain cells. Alternatively, JP Patent Publication (Kokai) No. 8-89239 A (1996) discloses a porous collagen sponge. It is known that the collagen sponge cannot uniformly distribute cells in a three-dimensional manner, possibly depending on its hydrophobicity or due to the heterogeneity of the material, though this cause is not clear. In addition, in the case where cells are cultured in advance and then transplanted, there also exists an approach called gel-embedding culture in which cells are embedded in a collagen gel and cultured. However, the cells are disproportionately located in the gel and nonuniformly distributed.

PRIOR ART DOCUMENTS

Patent Documents

Patent Document 1: JP Patent Publication (Kokai) No. 62-122586 A (1987)
Patent Document 2: JP Patent Publication (Kokai) No. 8-89239 A (1996)

Non Patent Documents

Non Patent Document 1: Journal of Neurosurgery 91 851-856, 1999
Non Patent Document 2: Motohiro Hirose and Hajime Ogushi, "Regenerative Medicine of Bone Using Regenerated Cultured Bone Tissues", The Tissue Engineering 2007, 178-183; 2007.7
Non Patent Document 3: Dental Outlook, 97 (3), 665-677, 2001

SUMMARY OF INVENTION

Object to be Solved by the Invention

An object to be solved by the present invention is to solve the above-described problems of the conventional techniques. Specifically, an object of the present invention is to provide a three-dimensional cell support that is capable of uniformly distributing cells and retaining the cells in a state without nonuniformity and is made of a biodegradable material. A further object of the present invention is to provide a bone regeneration material that serves as a scaffold matrix having, in itself, the ability to regenerate bone and to provide a bone regeneration material having the ability to regenerate bone, even when using a gelatin material, which is allegedly unsuitable for bone regeneration. A further object of the present invention is to provide a medical material using the cell support or the bone regeneration material as described above.

Means for Solving the Object

The present inventors have conducted diligent studies to attain the objects. The present inventors have used a cell-adhesive biodegradable material to produce a porous body having a predetermined porosity, average pore size, and water absorption rate and having a hole interconnecting pores, and examined cell distribution in this porous body by inoculating cells to the porous body. Consequently, it has been found that the cells are uniformly distributed in the porous body and that only a small number of cells drop from the porous body, while many cells are seen in the porous body. Moreover, the porous body produced using gelatin or recombinant gelatin has been evaluated for bone regeneration in a rat cranial defect model. Consequently, it has been found that the porous construct exhibits favorable bone regeneration. The present invention has been completed based on these findings.

The present invention provides a cell support consisting of a porous body made of a biodegradable material, the porous body having the following properties:
(a) a porosity from 81% to 99.99%,
(b) an average pore size of 10 to 400 μm,
(c) having a hole interconnecting pores, and
(d) a water absorption rate from 1000% to 9900%.

The present invention further provides a bone regeneration material consisting of a porous body made of a biodegradable material, the porous body having the following properties:
(a) a porosity from 81% to 99.99%,
(b) an average pore size of 10 to 400 μm,
(c) having a hole interconnecting pores, and
(d) a water absorption rate from 1000% to 9900%.

Preferably, the biodegradable material has a Grand average of hydropathicity (GRAVY) value from −5.0 to 0.3.

Preferably, the biodegradable material is at least one or more materials selected from protein, polypeptide, polylactic acid, polyglycolic acid, PLGA, chitin, chitosan, cellulose, and hyaluronic acid.

Preferably, the biodegradable material is natural or recombinant gelatin, natural or recombinant fibronectin, or natural or recombinant laminin.

Preferably, the biodegradable material is cross-linked.

Preferably, the cross-linking is performed with an aldehyde, a condensing agent, or an enzyme.

Preferably, the biodegradable material is recombinant gelatin.

Preferably, the recombinant gelatin is represented by the formula:

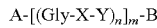

A-[(Gly-X-Y)$_n$]$_m$-B wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X-Y of total n may be the same as or different from each other.

Preferably, the recombinant gelatin is represented by the formula:

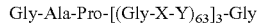

Gly-Ala-Pro-[(Gly-X-Y)$_{63}$]$_3$-Gly wherein each X of total 63 independently represents any amino acid; each Y of total 63 independently represents any amino acid; and each Gly-X-Y of total 63 may be the same as or different from each other.

Preferably, the recombinant gelatin has any of the followings:
(1) the amino acid sequence represented by SEQ ID NO: 1, or
(2) an amino acid sequence having 80% or higher homology to the amino acid sequence represented by SEQ ID NO: 1 and having biodegradability.

Preferably, the cell support of the present invention is produced by cross-linking the biodegradable material, followed by stirring and subsequent freeze drying.

The present invention further provides a regenerative medicine material comprising the aforementioned cell support of the present invention.

The present invention further provides a regenerative medicine material comprising the aforementioned cell support of the present invention and a cell graft.

Preferably, the bone regeneration material of the present invention is produced by cross-linking the biodegradable material, followed by stirring and subsequent freeze drying.

The present invention further provides a regenerative medicine material comprising the aforementioned bone regeneration material of the present invention.

The present invention further provides a regenerative medicine material comprising the aforementioned bone regeneration material of the present invention and a cell graft.

Effect of the Invention

The cell support of the present invention is a three-dimensional cell support that is capable of uniformly distributing and retaining cells and is made of a biodegradable material. The cell support of the present invention has, in itself, the ability to regenerate bone and can be used in bone regeneration treatment. In addition, even a gelatin material, which is allegedly unsuitable for bone regeneration, generally, can be provided as a scaffold construct having the ability to regenerate bone by imparting thereto the three-dimensional structure obtained during the course of the present invention. Use of the cell support of the present invention for regenerative medicine can achieve therapeutic effects prevented from being variable and can also overcome the problem of unexpected adverse effect.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 5 shows a photograph (Day 1) of a slice of a collagen sponge.

FIG. 6 shows a photograph (Day 4) of a slice of the collagen sponge.

FIG. 7 shows a photograph (Day 1) of a slice of the recombinant gelatin sponge (10%) (diameter: 8 mm, height: 5 mm).

FIG. 8 shows a photograph (Day 4) of a slice of the recombinant gelatin sponge (10%) (diameter: 8 mm, height: 5 mm).

FIG. 9 shows a photograph (Day 1) of a slice of an atelocollagen honeycomb sponge.

FIG. 10 shows a photograph (Day 4) of a slice of the atelocollagen honeycomb sponge.

FIG. 11 shows a photograph (Day 1) of a slice of the recombinant gelatin sponge (10%) (2 mm×2 mm×3 mm).

FIG. 12 shows a photograph (Day 4) of a slice of the recombinant gelatin sponge (10%) (2 mm×2 mm×3 mm).

FIG. 13 shows a photograph (Day 1) of a slice of collagen gel-embedding culture.

FIG. 14 shows a photograph (Day 4) of a slice of collagen gel-embedding culture.

FIG. 15 shows a photograph (Day 1) of a slice of culture on a collagen gel.

FIG. 16 shows a photograph (Day 4) of a slice of culture on the collagen gel.

FIG. 17 shows results of a cell adhesiveness test (DNA assay).

FIG. 18 shows results of a cell adhesiveness test (DNA assay).

FIG. 19 shows the manner of cell adhesion to a recombinant gelatin-coated plate.

EMBODIMENTS FOR CARRYING OUT THE INVENTION

Figure 1:
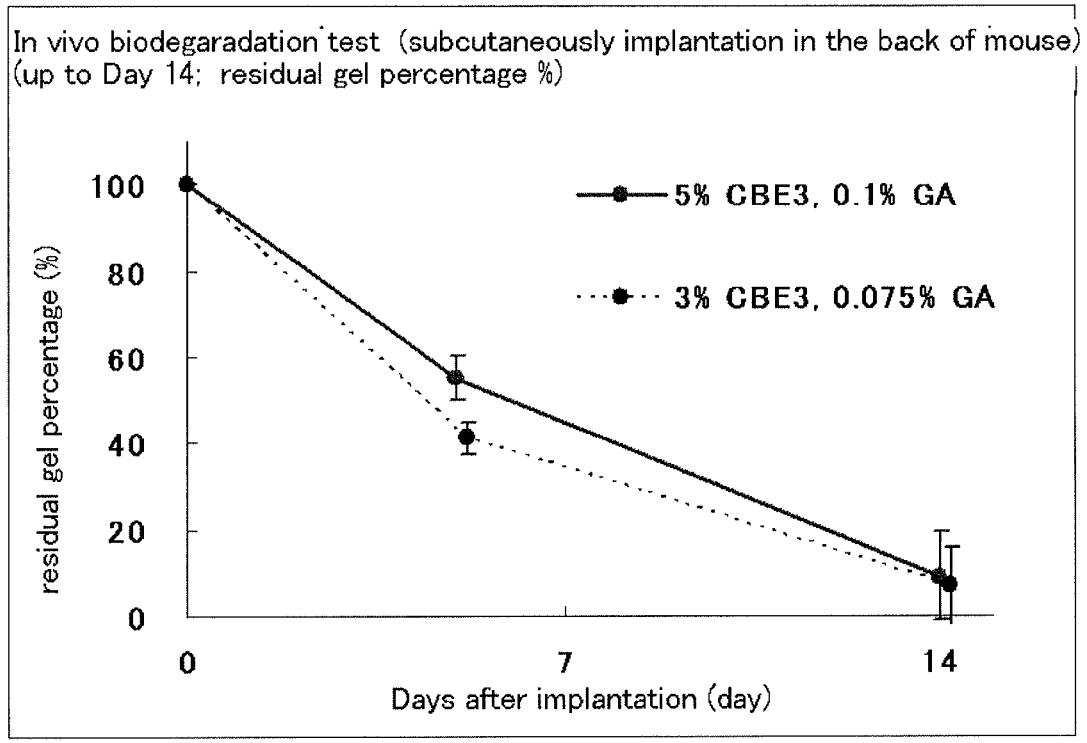
FIG. 1 shows results of subcutaneously implanting a recombinant gelatin hydrogel into the back of mouse and measuring the amount of residual gel over time.

Hereinafter, the embodiments of the present invention will be described in detail.

(1) Biodegradable Material (1-1) Type of Biodegradable Material

The cell support of the present invention is made of at least one or more biodegradable materials. The biodegradable material used in the present invention is not particularly limited by its type as long as it is degraded in vivo. For the biodegradable material used in the present invention, it is preferred that an index for hydrophilicity and hydrophobicity indicated by Grand average of hydropathicity (GRAVY) value should be from −5.0 to 0.3, more preferably from −3.0 to 0.0. A hydrophilic polypeptide satisfying this range is particularly preferable. The Grand average of hydropathicity (GRAVY) value can be obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

As a specific example of the biodegradable material, at least one or more materials selected from protein, polypeptide, polylactic acid, polyglycolic acid, PLGA, chitin, chitosan, cellulose, and hyaluronic acid is preferably used. Among them, protein or polypeptide is preferable. Particularly, gelatin, fibronectin, or laminin, or the like is preferable. These proteins may be a recombinant protein or may be a natural protein. Specific examples of the recombinant proteins include recombinant gelatin, ProNectin, recombinant fibronectin, and recombinant laminin. Among them, recombinant gelatin is most preferable. The recombinant gelatin will be described later in the present specification.

It is preferred that the biodegradable material used in the present invention should have cell adhesiveness. This is because use of a material having high cell adhesiveness is considered to be able to prevent the leakage or nonuniform distribution of cells. Although the cell adhesiveness is difficult to quantitatively describe, these polymer materials may be given a contrivance to enhance cell adhesiveness. Methods such as [1] "coating of matrix surface with a cell-adhesive substrate (fibronectin, vitronectin, and laminin) or a cell adhesion sequence (RGD sequence, LDV sequence, REDV sequence, YIGSR sequence, PDSGR sequence, RYVVLPR sequence, LGTIPG sequence, RNIAEIIKDI sequence, IKVAV sequence, LRE sequence, DGEA sequence, and HAV sequence, indicated by single letter codes for amino acids) peptide", [2] "amination or cationization of matrix surface", and [3] "plasma treatment or corona discharge-based hydrophilic treatment of matrix surface" may be used as specific methods.

(1-2) Cross-Linking

The biodegradable material used in the present invention may be cross-linked or may not be cross-linked. Those cross-linked are preferable. A method known in the art, such as thermal cross-linking, chemical cross-linking, cross-linking using an aldehyde (e.g., formaldehyde and glutaraldehyde), cross-linking using a condensing agent (carbodiimide, cyanamide, etc.), enzymatic cross-linking, photocrosslinking, UV cross-linking, hydrophobic interaction, hydrogen bond, or ionic interaction can be used as a cross-linking method. A cross-linking method using glutaraldehyde is most preferred.

Examples of the photocrosslinking include those based on light irradiation of a polymer containing a photoreactive group introduced therein, or light irradiation in the presence of a photosensitizer. Examples of the photoreactive group include a cinnamyl group, a coumarin group, a dithiocarbamyl group, a xanthene dye, and camphorquinone.

In the case of performing cross-linking using an enzyme, the enzyme is not particularly limited as long as it has the effect of cross-linking between the biodegradable materials. The cross-linking can be performed using preferably transglutaminase and laccase, most preferably transglutaminase. Specific examples of proteins that may be subjected to enzymatic cross-linking with transglutaminase are not particularly limited as long as they are proteins having a lysine residue and a glutamine residue. The transglutaminase may be derived from a mammal or may be derived from a microbe. Specific examples thereof include ACTIVA series manufactured by Ajinomoto Co., Inc., mammal-derived transglutaminase sold as reagents, for example, guinea pig liver-derived transglutaminase, goat-derived transglutaminase, and rabbit-derived transglutaminase manufactured by Oriental Yeast Co., ltd., Upstate USA Inc., or Biodesign International, and human-derived blood coagulation factor (Factor XIIIa, Haematologic Technologies, Inc.).

The cross-linking of the biodegradable material involves two steps: the step of mixing a biodegradable material solution with a cross-linking agent and the step of reacting the homogeneous solution.

In the present invention, the mixing temperature for the treatment of biodegradable material with a cross-linking agent is not particularly limited as long as the solution can be homogeneously stirred. The temperature is preferably 0° C. to 40° C., further preferably 0° C. to 30° C., further preferably 3° C. to 25° C., further preferably 3° C. to 15° C., further preferably 3° C. to 10° C., particularly preferably 3° C. to 7° C.

The temperature can be raised after the biodegradable material and the cross-linking agent is stirred. The reaction temperature is not particularly limited as long as the cross-linking proceeds. In consideration of the denaturation or degradation of the biodegradable materials, the temperature is substantially 0° C. to 60° C., more preferably 0° C. to 40° C., further preferably 3° C. to 25° C., further preferably 3° C. to 15° C., further preferably 3° C. to 10° C., particularly preferably 3° C. to 7° C.

(1-3) Recombinant Gelatin

The recombinant gelatin which can be used in the present invention preferably has repeats of the sequence represented by Gly-X-Y (X and Y each independently represent any amino acid) characteristic of collagen (a plurality of Gly-X-Y sequences may be the same as or different from each other). Preferably, two or more sequences of cell adhesion signals are contained in a molecule. A recombinant peptide having an amino acid sequence derived from a partial amino acid sequence of collagen can be used as the recombinant gelation used in the present invention. For example, those described in EP1014176, U.S. Pat. No. 6,992,172, WO2004/85473, and WO2008/103041 can be used, though the recombinant gelatin is not limited to them. A preferable recombinant peptide used in the present invention is a recombinant peptide having the following aspect.

The recombinant gelatin used in the present invention is excellent in biocompatibility based on the original performance of natural gelatin, is free from concerns about BSE or the like because of being not naturally derived, and is also excellent in non-infectious properties. Moreover, since the recombinant gelatin used in the present invention is homogeneous compared with natural one and its sequence is determined, it can be designed precisely with a little variation in strength or degradability depending on cross-linking or the like described later.

The molecular weight of the recombinant gelatin is preferably from 2 KDa to 100 KDa, more preferably from 2.5 KDa to 95 KDa, further preferably from 5 KDa to 90 KDa, most preferably from 10 KDa to 90 KDa.

The recombinant gelatin has repeats of the sequence represented by Gly-X-Y characteristic of collagen. In this context, a plurality of Gly-X-Y sequences may be the same as or different from each other. In Gly-X-Y, Gly represents glycine, and X and Y each represent any amino acid (preferably, any amino acid other than glycine). The GXY sequence characteristic of collagen is a very specific partial structure in the amino acid composition and sequence of gelatin/collagen, compared with other proteins. In this moiety, glycine accounts for approximately ⅓ of the whole and appears at a rate of one out of three amino acids in the amino acid sequence. Glycine is the simplest amino acid. Its position in the molecular chain is less restricted, and glycine makes a significant contribution to the regeneration of the helix structure during gelatinization. It is preferred that imino acids (proline or oxyproline) should be included in large amounts in the amino acids represented by X and Y and account for 10% to 45% of all the amino acids. It is preferred that preferably 80% or more, more preferably 95% or more, most preferably 99% or more of the amino acids in the sequence should form the GXY repeat structures.

In general gelatin, of polar amino acids, those having an electric charge and those uncharged are present at a 1:1 ratio. In this context, the polar amino acids specifically refer to cysteine, aspartic acid, glutamic acid, histidine, lysine, asparagine, glutamine, serine, threonine, tyrosine, and arginine. Of them, polar uncharged amino acids refer to cysteine, asparagine, glutamine, serine, threonine, and tyrosine. The ratio of the polar amino acids is 10 to 40%, preferably 20 to 30%, to all amino acids constituting the recombinant gelatin used in the present invention. In addition, it is preferred that the ratio of uncharged amino acids to the polar amino acids should be from 5% to less than 20%, preferably less than 10%. It is further preferred that any one amino acid, preferably two or more amino acids which are selected from serine, threonine, asparagine, tyrosine and cysteine should not be contained in the sequence.

In general, minimal ammo acid sequences that function as cell adhesion signals in polypeptides are known (e.g., "Medicina Philosophica", Vol. 9, No. 7 (1990), p. 527, Nagai Shoten Co., Ltd.). It is preferred that the recombinant gelatin used in the present invention should have two or more of these cell adhesion signals in a molecule. Specific sequences are preferably RGD sequences, LDV sequences, REDV sequences, YIGSR sequences, PDSGR sequences, RYVV-LPR sequences, LGTIPG sequences, RNIAEIIKDI sequences, IKVAV sequences, LRE sequences, DGEA sequences, and HAV sequences, more preferably RGD sequences, YIGSR sequences, PDSGR sequences, LGTIPG sequences, IKVAV sequences, and HAV sequences, particularly preferably RGD sequences, indicated by single letter codes for amino acids, in terms that many types of cells can adhere thereto. Of the RGD sequences, an ERGD sequence is preferable.

For the arrangement of the RGD sequences in the recombinant gelatin used in the present invention, it is preferred that the number of amino acids between the RGD sequences should be between 0 and 100, preferably between 25 and 60, and should not be uniformly determined.

From the viewpoint of cell adhesion/growth, the content of this minimal amino acid sequence is preferably 3 to 50 sequences, more preferably 4 to 30 sequences, particularly preferably 5 to 20 sequences, most preferably 12 sequences, per protein molecule.

In the recombinant gelatin used in the present invention, the ratio of the RGD motifs to the total number of the amino acids is preferably at least 0.4%. In the case where the recombinant gelatin contains 350 or more amino acids, it is preferred that each stretch of 350 amino acids should contain at least one RGD motif. The ratio of the RGD motifs to the total number of the amino acids is more preferably at least 0.6%, further preferably at least 0.8%, further preferably at least 1.0%, further preferably at least 1.2%, most preferably at least 1.5%. The number of the RGD motifs within the recombinant gelatin is preferably at least 4, more preferably 6, further preferably 8, further preferably from 12 to 16, per 250 amino acids. The ratio of the RGD motifs of 0.4% corresponds to at least one RGD sequence per 250 ammo acids. Since the number of the RGD motifs is an integer, gelatin consisting of 251 amino acids must contain at least two RGD sequences in order to satisfy the feature of 0.4%. Preferably, the recombinant gelatin of the present invention contains at least two RGD sequences per 250 amino acids, more preferably at least three RGD sequences per 250 amino acids, further preferably at least four RGD sequences per 250 amino acids. In a further aspect, the recombinant gelatin of the present invention comprises at least 4 RGD motifs, preferably 6, more preferably 8, further preferably 12 to 16 RGD motifs.

Moreover, the recombinant gelatin may be partially hydrolyzed.

It is preferred that the recombinant gelatin used in the present invention should have repeat structures represented by A[(Gly-X-Y)n]mB. m is preferably 2 to 10, more preferably 3 to 5. n is preferably 3 to 100, more preferably 15 to 70, most preferably 50 to It is preferred that a plurality of naturally occurring collagen sequence units should be bonded to repeat units. In this context, the naturally occurring collagen may be any naturally occurring collagen and is preferably type-I, type-II, type-III, type-IV, and type-V collagens, more preferably type-I, type-II, and type-III collagens. In another embodiment, the origin of the collagen is preferably a human, cattle, a pig, a mouse, or a rat, more preferably a human.

The isoelectric point of the recombinant gelatin used in the present invention is preferably 5 to 10, more preferably 6 to 10, further preferably 7 to 9.5.

Preferably, the recombinant gelatin is not deaminated.

Preferably, the recombinant gelatin does not have telopeptide.

Preferably, the recombinant gelatin is a substantially pure collagen material which is prepared from a nucleic acid encoding natural collagen.

The recombinant gelatin used in the present invention is particularly preferably a recombinant peptide having any of the followings:
(1) the amino acid sequence represented by SEQ ID NO: 1; or
(2) an amino acid sequence having 80% or higher (more preferably 90% or higher, most preferably 95% or higher) homology to the amino acid sequence represented by SEQ ID NO: 1 and having biodegradability.

The recombinant gelatin used in the present invention can be produced by a gene recombination technique known by those skilled in the art and can be produced according to a method described in, for example, EP1014176A2, U.S. Pat. No. 6,992,172, WO2004-85473, or WO2008/103041. Specifically, a gene encoding the amino acid sequence of the predetermined recombinant gelatin is obtained, and this is incorporated in an expression vector to prepare a recombinant expression vector, which is then introduced in appropriate hosts to prepare transformants. The obtained transformants are cultured in an appropriate medium, whereby the recombinant gelatin is produced. Thus, the produced recombinant gelatin can be collected from the cultures to prepare the recombinant gelatin used in the present invention.

(2) Porous Body

The cell support of the present invention consists of a porous body made of a biodegradable material, the porous body having the following properties:

(a) Porosity

For the porosity of the cell support (porous body) of the present invention, a bulk density ($\rho$) and a true density ($\rho c$) are measured to determine the porosity ($P=1-\rho/\rho c$ (%)). The bulk density ($\rho$) can be calculated from its dry weight and volume. The true density ($\rho c$) can be determined by a Hubbard-type specific gravity bottle method. The porosity of the cell support (porous body) of the present invention is from 81% to 99.99%, preferably from 95.01% to 99.9%.

(b) Average Pore Size

The average pore size of the cell support (porous body) of the present invention is determined by observing its internal cross-sectional structure with a scanning electron microscope. The average pore size of the cell support (porous body) of the present invention is 10 to 400 µm, preferably 50 to 300 µm, more preferably 70 to 200 µm.

(c) Hole Interconnecting Pores

A hole interconnecting pores is present in the cell support of the present invention. The presence of the hole interconnecting pores allows pores to continue from the outside of the sponge through the deep portion of the sponge, whereby cells inoculated in the sponge can be dispersed or diffused into the inside of the sponge. Moreover, the hole interconnecting pores is preferably 10 µm or larger for exerting the function.

(d) Water Absorption Rate

The water absorption rate of the cell support (porous body) of the present invention can be calculated according to ($W1\div W0\times 100(\%)$) using a dry weight (W0) and a weight (W1) at the time of water swelling after 5-minute spontaneous absorption of ultrapure water at 25° C. and sufficient removal of redundant water on a plastic petri dish. The water absorption rate of the cell support (porous body) of the present invention is from 1000% to 9900%, preferably from 2000% to 5000%.

The porous body made of a biodegradable material can be produced using a method known in the art. For example, the biodegradable material described above can be cross-linked by the method described above, followed by stirring using a homogenizer and subsequent freeze drying to produce the porous body made of a biodegradable material.

(3) Application of Cell Support

The cell support of the present invention can be used as a scaffold matrix or a therapeutic agent for bone regeneration treatment. The cell support of the present invention can be used alone as an agent for bone regeneration treatment. A disease is not limited as long as it is subjected to treatment requiring bone regeneration or new bone formation. In addition, the cell support of the present invention can also be used as an agent for bone regeneration treatment in combination with a cell graft or an osteoinductive agent. Examples of the osteoinductive agent include, but not particularly limited to, BMP (bone morphogenetic protein) and bFGF (basic fibroblast growth factor).

Moreover, the cell support of the present invention can be used as a scaffold for transplanting cells to organisms for the purpose of regenerative medicine. Specifically, the cell support of the present invention can be used as a regenerative medicine material. In the case of using the cell support of the present invention as a regenerative medicine material, cells are inoculated to the cell support of the present invention, and the cell support incorporating the cells therein can be transplanted to organisms. Specifically, the cell support of the present invention comprising a cell graft can be used as a regenerative medicine material. However, the application of the cell support of the present invention is not limited to the regenerative medicine, and the cell support of the present invention may be used in the culture of cells that are not intended for transplantation.

The cells to be supported by the cell support of the present invention can be selected appropriately according to the purpose and are not particularly limited by their types. Preferably, animal cells can be used, and, particularly, human-derived cells can be used. The type of the animal cells (particularly, human-derived cells) may be any of pluripotent cells, somatic stem cells, precursor cells, and mature cells. For example, ES cells, GS cells, or iPS cells can be used as pluripotent cells. For example, mesenchymal stem cells (MSCs), hematopoietic stem cells, or neural stem cells can be used as somatic stem cells. For example, cells derived from the skin, dermis, epidermis, muscle, cardiac muscle, nerve, bone, cartilage, endothelium, brain, epithelium, heart, kidney, liver, pancreas, spleen, oral cavity, cornea, or hair can be used as precursor cells and mature cells. One example of most preferable cells among these cells includes cartilage cells. For example, ES cells, iPS cells, MSCs, cartilage cells, osteoblasts, osteoprogenitor cells, mesenchyme cells, myoblasts, cardiac muscle cells, nerve cells, hepatic cells, beta cells, fibroblasts, corneal endothelial cells, vascular endothelial cells, corneal epithelial cells, or hematopoietic stem cells can be used as human-derived cells. For therapeutic application, host-derived cells may be used or a heterogeneous cell graft may be used. Moreover, the origin of the cells may be any of autologous cells and heterologous cells.

In the case where cell inoculation to the cell support of the present invention is required, this cell inoculation can be performed by a routine method. Cells, for example, in a suspension form, may be inoculated to the cell support of the present invention placed in an appropriate container.

Hereinafter, the present invention will be described more specifically with reference to Examples. However, the present invention is not intended to be limited to Examples.

EXAMPLES

Example 1

Recombinant Gelatin

CBE3 described below was prepared as a recombinant gelatin (described in WO2008-103041).
CBE3
Molecular weight: 51.6 kD
Structure: GAP[(GXY)63]3G
The number of amino acids: 571
The number of RGD sequences: 12
Imino acid content: 33%
Substantially 100% of amino acids are derived from the GXY repeat structures. The amino acid sequence of CBE3 does not contain serine, threonine, asparagine, tyrosine, and cysteine.
CBE3 has an ERGD sequence.
Isoelectric point: 9.34
Amino acid sequence (SEQ ID NO: 1 in the Sequence Listing) (same as SEQ ID NO: 3 in WO2008/103041 except that X at the end was modified to "P")

GAP (GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP) 3G

Example 2

Results of Calculating GRAVY of Recombinant Gelatin

A Grand average of hydropathicity (GRAVY) value serving as an index for hydrophilicity and hydrophobicity of protein/polypeptide was determined for the recombinant gelatin CBE3. The GRAVY value was obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)". As a result, the GRAVY value of the recombinant gelatin CBE3 was −0.682, showing that it was a highly hydrophilic material.

Example 3

Degradation of Recombinant Gelatin in Mouse Skin

In order to prove the biodegradability of the recombinant gelatin CBE3 in vivo, its subcutaneous degradability in mice was examined. The recombinant gelatin CBE3 was cross-linked using glutaraldehyde (GA) to prepare recombinant gelatin CBE3 hydrogels (gel in which 5% CBE3 was cross-linked using 0.1% GA and gel in which 3% CBE3 was cross-linked using 0.075% GA). Each obtained hydrogel was subcutaneously implanted into the back of each DDY mouse (male, 8 weeks old), and time-dependent change in pathological slice and the amount of residual gel were measured.

Figure 2:
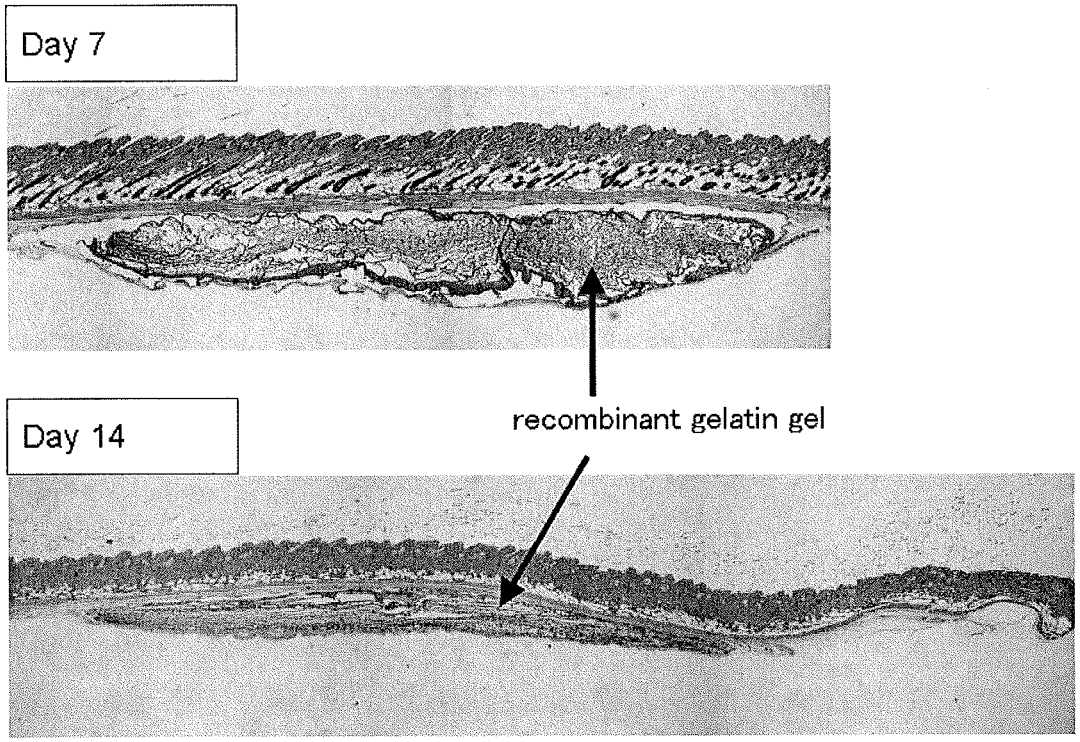
FIG. 2 shows an image (hematoxylin-eosin staining) of a pathological slice from the back of mouse in which the recombinant gelatin hydrogel has been implanted subcutaneously.

For the amount of residual gel, each gel was taken out after a lapse of the test period and freeze-dried, and the dry weight of residual gel was compared with the initial dry weight of the implant. The results are shown in FIG. 1. As is evident from the results shown in FIG. 1, the residual amount of the gel in which 5% CBE3 was cross-linked using 0.1% GA was 55% in 5 days and 9% in 14 days with respect to the implant, showing that the gel was gradually degraded in vivo. Also, the residual amount of the gel in which 3% CBE3 was cross-linked using 0.075% GA was 41% in 5.2 days and 7% in 14.2 days, showing that the gel was gradually degraded in vivo. Moreover, a typical image (hematoxylin-eosin staining) of a pathological slice is shown in FIG. 2. The manner in which the recombinant gelatin CBE3 gel was gradually degraded and became small is shown. These results demonstrated that a matrix prepared with recombinant gelatin as a material had biodegradability.

Example 4

Preparation of Recombinant Gelatin Sponge (Porous Body)

Sponges (porous bodies) were prepared using the recombinant gelatin CBE3. In this Example, 10% CBE3 and 5% CBE3 were used, respectively, in the preparation. Each solution is prepared according to composition shown below. After addition of glutaraldehyde, the mixture is stirred at 17,000 rpm at 4° C. for 4 minutes using a homogenizer (AM-11, manufactured by Nippon Seiki Co., Ltd.) and directly cooled rapidly at −80° C. for 3 hours.
Composition:
10 mL of 5% sponge (CBE3: 500 mg, ultrapure water: 9424 µL, 1 N HCl: 76 µL, 3% glutaraldehyde: 500 µL)
10 mL of 10% sponge (CBE3: 1 g, ultrapure water: 9348 µL, 1 N HCl: 152 µL, 3% glutaraldehyde: 500 µL)
Then, a product obtained by standing at 4° C. for 16 hours is shaken for 4 hours in a sufficient amount of a 0.2 M glycine solution of 37° C. Then, washing with 10 L of ultrapure water is repeated 8 times (a total of 4 hours), and the resulting product is frozen at −80° C. for 2 hours. Then, freeze drying was performed for 4 days in a freeze drier to obtain recombinant gelatin sponges (porous bodies).

Example 5

Measurement of Porosity of Recombinant Gelatin Sponge

A porosity was measured for the recombinant gelatin sponges obtained in Example 4. For the measurement, a bulk density ($\rho$) and a true density ($\rho c$) were measured to determine the porosity ($P=1-\rho/\rho c$ (%)). The bulk density ($\rho$) of each recombinant gelatin sponge was calculated from its dry weight and volume. The true density ($\rho c$) was determined by a Hubbard-type specific gravity bottle method. Results from the number of samples (N)=4 showed that the 5% sponge achieved a bulk density of 0.03 g/cm$^3$, a true density of 1.01 g/cm$^3$, and a porosity of 97% (CV value of 7%). The results also showed that the 10% sponge achieved a bulk density of 0.05 g/cm$^3$, a true density of 1.23 g/cm$^3$, and a porosity of 96% (CV value of 8%).

Example 6

Measurement of Water Absorption Rate of Recombinant Gelatin Sponge

A water absorption rate was measured for the recombinant gelatin sponges obtained in Example 4. The water absorption rate was calculated according to (W1÷W0×100(%)) using a dry weight (W0) and a weight (W1) at the time of water swelling after 5-minute spontaneous absorption of ultrapure water at 25° C. and sufficient removal of redundant water on a plastic petri dish. As a result, the water absorption rate of the 5% sponge was 3640(%) on average from the number of samples (N)=5, showing that it had a high water absorption rate.

Example 7

Figure 3:
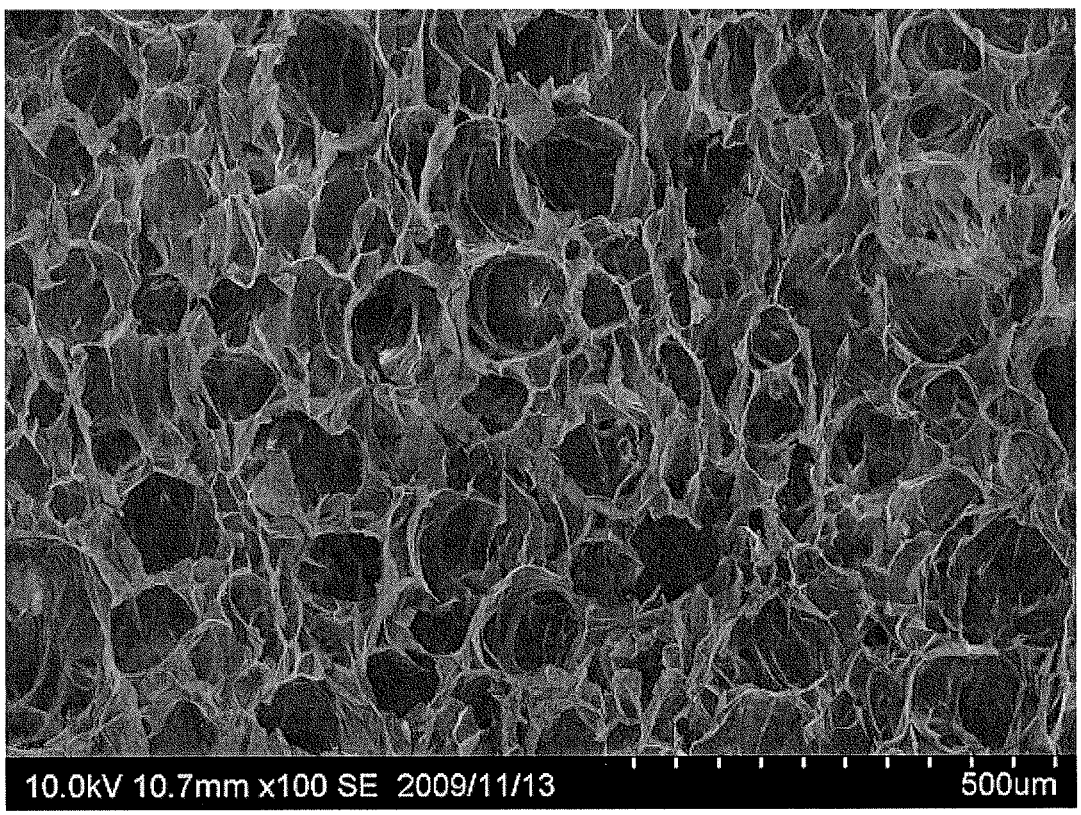
FIG. 3 shows an image of the internal cross-sectional structure of a recombinant gelatin sponge (cross section of 5% sponge) observed with a scanning electron microscope.
Figure 4:
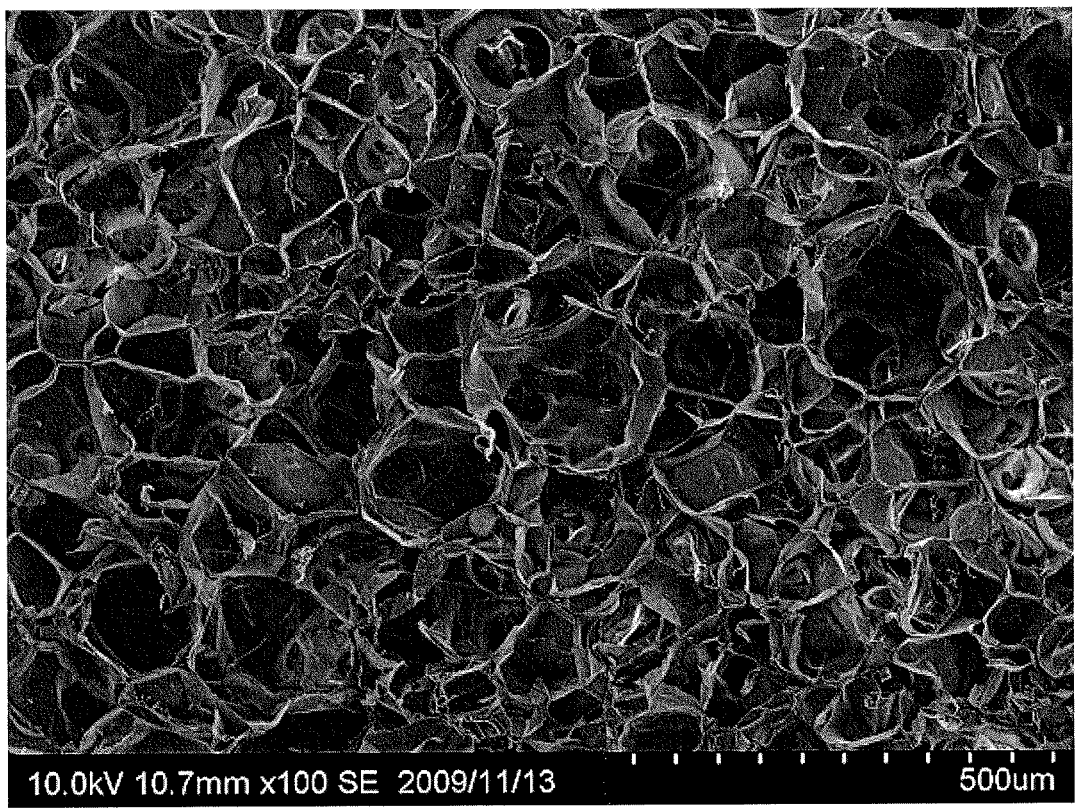
FIG. 4 shows an image of the internal cross-sectional structure of a recombinant gelatin sponge (cross section of 10% sponge) observed with a scanning electron microscope.

SEM Image of Recombinant Gelatin Sponge and Measurement of Average Pore Size An internal cross-sectional structure was observed for the recombinant gelatin sponges obtained in Example 4 with a scanning electron microscope. A typical SEM image is shown in FIGS. 3 (cross section of 5% sponge) and 4 (cross section of 10% sponge). This showed the porous internal structure of the obtained recombinant gelatin sponge. The internal pore size was 106.0±7.7 μm (on average from the number of pores on diameter) for the 10% sponge and 114.8±15.8 μm for the 5% sponge. As is also evident from FIGS. 3 and 4, a hole interconnecting pores is present between the pores and thereby allows pores to continue from the outside of the sponge through the deep portion of the sponge. Moreover, this hole interconnecting pores can be confirmed to be 10 μm or larger in size, also showing that cells can pass through the interconnecting hole. These results demonstrate that cells inoculated in the sponge can be dispersed or diffused into the inside of the sponge.

Example 8

Comparison of Cell Distribution Between in Collagen Sponge and in Recombinant Gelatin Sponge The recombinant gelatin sponges (5% and 10%) of the present invention obtained in Example 4 and a collagen sponge (Nitta Gelatin Inc.; for 35 mm dishes) for comparison were separately molded into the same shape (cylindrical shape of 8 mm in diameter and 5 mm in height), and cells were inoculated from above each sponge in a 24-well culture plate. The inoculated cells were human mesenchymal stem cells (hMSCs). These cells were suspended at a concentration of 8000000 cells/mL in a medium (Takara Bio Inc.; MSCGM-CD™ BulletKit™), and the suspension (250 μL) was inoculated to the sponge. After standing for 2 hours, a medium was added to the bottom of the plate, and the cells were cultured until Day 1 or Day 4. As a result, many of the cells inoculated to the collagen sponge passed through the sponge and fell to the bottom, whereas only a small number of cells dropped to the bottom from the recombinant gelatin sponge.

Moreover, each cell-inoculated sponge was washed with PBS, then fixed in 10% formaldehyde, and embedded in paraffin to prepare a tissue slice. Staining was performed by HE staining to visualize cell distribution within the sponge (FIGS. 5, 6, 7, and 8). As a result, cell distribution was nonuniform in the collagen sponge for comparison. For the recombinant gelatin sponge of the present invention, the cells were uniformly distributed in the sponge, and it was revealed that only a small number of cells dropped from the sponge, while many cells were seen in the sponge. In this context, each slice photograph was divided into zones, and the number of cells present in each zone was counted and then divided by an area occupied on each zone (within the sponge) to determine the number of cells per unit area. The variability of the determined number of cells per unit area is shown in FIGS. 5, 6, 7, and 8 in terms of CV value. Uniform or nonuniform distribution can be determined on the basis of this CV value of variability. It is quantitatively shown that distribution was very nonuniform in the collagen sponge with CV values of 45% at Day 1 and 56% at Day 4, whereas distribution was uniform in the recombinant gelatin sponge with CV values of 29% at Day 1 and 30% at Day 4. Moreover, for the collagen sponge, it was confirmed that the sponge itself became disadvantageously deformed with the passage of the culture time. On the other hand, for the recombinant gelatin sponge, it could be confirmed the sponge itself reliably maintained its shape.

Example 9

Comparison of Cell Distribution Between in Atelocollagen Sponge (Honeycomb) and in Recombinant Gelatin Sponge The recombinant gelatin sponges (5% and 10%) of the present invention obtained in Example 4 and an atelocollagen honeycomb sponge (Koken Co., Ltd.) for comparison were separately molded into the same shape (3 mm×2 mm×2 mm rectangular shape), and cells were inoculated to the upper side of the sponge in a 24-well culture plate. The inoculated cells were human mesenchymal stem cells (hMSCs). These cells were suspended at a concentration of 8,000,000 cells/mL in a medium (Takara Bio Inc.; MSCGM-CD™ BulletKit™), and the suspension (12 μL) was inoculated to the sponge. After standing for 2 hours, a medium was added to the bottom of the plate, and the cells were cultured until Day 1 or Day 4. As a result, many of the cells inoculated to the atelocollagen honeycomb sponge for comparison passed through the sponge and fell to the bottom, whereas only a small number of cells dropped to the bottom from the recombinant gelatin sponge.

Moreover, each cell-inoculated sponge was washed with PBS, then fixed in 10% formaldehyde, and embedded in paraffin to prepare a tissue slice. Staining was performed by HE staining to visualize cell distribution within the sponge (FIGS. 9, 10, 11, and 12). As a result, cell distribution was nonuniform in the atelocollagen honeycomb sponge for comparison. For the recombinant gelatin sponge of the present invention, the cells were uniformly distributed in the sponge, and it was revealed that only a small number of cells dropped from the sponge, while many cells were seen in the sponge. In this context, each slice photograph was divided into zones, and the number of cells present in each zone was counted and then divided by an area occupied on each zone (within the sponge) to determine the number of cells per unit area. The variability of the determined number of cells per unit area is shown in FIGS. 9, 10, 11, and 12 in terms of CV value. Uniform or nonuniform distribution can be determined on the basis of this CV value of variability. It is quantitatively shown that distribution was very nonuniform in the atelocollagen honeycomb sponge with CV values of 66% at Day 1 and 79% at Day 4, whereas distribution was uniform in the recombinant gelatin sponge with CV values of 27% at Day 1 and 18% at Day 4.

Comparative Example 1

Collagen Gel-Embedding Culture Method (for Comparison)

Collagen gel-embedding culture was carried out for comparison with cell distribution/cell culture in the recombinant gelatin sponge of the present invention. The shape was the same cylindrical shape as in Example 8 to carry out the culture. A 0.5% atelocollagen solution (Koken Co., Ltd.; IPC-50, AteloCell) was mixed with a medium (Takara Bio Inc.; MSCGM-CD™ BulletKit™) at a ratio of 1:1 on ice at 4° C. to prepare a mixed medium. Human mesenchymal stem cells (hMSCs) were suspended at a concentration of 8000000 cells/mL in the mixed medium, and the suspension (500 µL) was inoculated to a 48-well plate. A gel was formed by standing at 37° C. for 30 minutes in 5% $CO_2$. Then, a sufficient amount of a medium was added thereto, and the cells were cultured for 4 days (Day 4). During the culture, the medium was replaced by a fresh medium every day. A sample of Day 4 was fixed in formalin and embedded in paraffin to prepare a slice. Staining was performed by HE staining to visualize internal cell distribution (FIGS. 13 and 14). In this context, each slice photograph was divided into zones, and the number of cells present in each zone was counted and then divided by an area occupied on each zone (within the sponge) to determine the number of cells per unit area. The variability of the determined number of cells per unit area is shown in FIGS. 13 and 14 in terms of CV value. Uniform or nonuniform distribution can be determined on the basis of this CV value of variability. Atelocollagen gel-embedding culture resulted in very nonuniform distribution with CV values of 45% at Day 1 and 51% at Day 4. The results showed that cells cultured in the atelocollagen gel fell in a heterogeneous state. Nonuniform cell distribution in the gel, which is a problem associated with the conventional technique collagen gel-embedding culture, was reproduced. Moreover, for the collagen gel-embedding, it was confirmed that the gel itself became disadvantageously deformed with the passage of the culture time.

Comparative Example 2

Cell Inoculation/Cell Culture on Collagen (for Comparison)

Cell inoculation/cell culture on a collagen gel was carried out for comparison with cell distribution/cell culture in the recombinant gelatin sponge of the present invention. The shape was the same cylindrical shape as in Example 8 to carry out the inoculation/culture. A 0.5% atelocollagen solution (Koken Co., Ltd.; IPC-50, AteloCell) was mixed with a medium (Takara Bio Inc.; MSCGM-CD™ BulletKit™) on ice at 4° C. to prepare a mixed medium. The mixed medium (500 µL) was added to a 48-well plate. A collagen gel was obtained by standing at 37° C. for 30 minutes in 5% $CO_2$. 500 µL of an 8,000,000 cells/mL hMSC cell suspension was inoculated onto this collagen gel and cultured for 4 days (Day 4). During the culture, the medium was replaced by a fresh medium every day. A sample of Day 4 was fixed in formalin and embedded in paraffin to prepare a slice. Staining was performed by HE staining to visualize internal cell distribution (FIGS. 15 and 16). As a result, cells inoculated/cultured on the atelocollagen gel failed to move from on the gel into the gel and did not exhibit uniform distribution in the gel.

Example 10

Cell Adhesiveness Test

A factor responsible for allowing cells to be uniformly distributed in the recombinant gelatin sponge is considered to be cell adhesiveness possessed by the recombinant gelatin. This is because the high cell adhesiveness of the recombinant gelatin is considered to be able to prevent the leakage or nonuniform distribution of cells. Thus, in order to examine the cell adhesiveness of the recombinant gelatin, a test was conducted on the adhesiveness of the recombinant gelatin CBE3 to cells.

The cells used were HUVECs (normal human umbilical vein endothelial cells; Takara Bio Inc.). HUVECs are generally known as cells to which various matrices exhibit poor cell adhesion. Endothelial Cell Basal Medium-2 (serum-free) (EBM™-2) and Endothelial Cell Growth Medium Kit-2 (2% FBS) (EGM™-2 BulletKit™) were used (Takara Bio Inc.) in the culture of HUVECs. An EDTA-containing 0.25% trypsin solution was used at the time of subculture and cell dissociation. HUVECs grown into a sufficient amount in a T-75 flask were dissociated from the bottom of the flask, and a supernatant was removed by centrifugation. Then, the cells were washed with the Endothelial Cell Basal Medium-2 containing the Endothelial Cell Growth Medium Kit-2, and a supernatant was removed again by centrifugation. The cells were suspended by the addition of a solution which was prepared by adding 0.1% BSA to the Endothelial Cell Basal Medium-2 free from the Endothelial Cell Growth Medium Kit-2. The number of live cells was counted using a cell counter, and the final cell concentration was adjusted to 500,000 cells/mL.

Meanwhile, for a comparison test of cell adhesiveness, plates coated with various proteins (recombinant gelatin CBE3, fibronectin, collagen manufactured by Fibrogen, Inc. (hereinafter, referred to as Fibrogen), pork skin-derived gelatin (hereinafter, referred to as PSK), and beef bone-derived gelatin (hereinafter, referred to as G1917P)) were prepared. The recombinant gelatin CBE3 was dissolved at a concentration of 1 mg/mL in PBS (phosphate-buffered saline) to prepare a recombinant gelatin CBE3 solution. Fibronectin was dissolved at a concentration of 1 mg/mL in PBS (phosphate-buffered saline) to prepare a fibronectin solution. Fibrogen was dissolved at a concentration of 1 mg/mL in PBS (phosphate-buffered saline) to prepare a Fibrogen solution. PSK was dissolved at a concentration of 1 mg/mL in PBS (phosphate-buffered saline) to prepare a PSK solution. G1917P was dissolved at a concentration of 1 mg/mL in PBS (phosphate-buffered saline) to prepare a G1917P solution. These solutions were diluted with PBS whenever necessary and used for addition to plates.

Non-treated 96-well plates (IWAKI) were used as plates. A solution containing each of the solutions diluted to a protein concentration of 0.02, 0.1, 0.2, or 2.0 µg/well with PBS was added in an amount of 50 µL/well to the Non-treated 96-well plate. Then, after incubation at 37° C. for 2 hours and removal of the solution, each well was washed by the addition of 100 µL of PBS, and this PBS was removed (washing step). This washing step was performed three times. As a result, coated plates differing in coating protein and coating concentration were obtained.

The HUVEC suspension (500,000 cells/mL) prepared above was inoculated in an amount of 100 µL/well to these coated plates. After incubation at 37° C. for 1 hour, the medium was removed by aspiration, each well was washed by the addition of 100 µL of PBS, and this PBS was removed by aspiration (PBS washing). This PBS washing was performed three times to obtain plates in a PBS-free state.

The number of cells on each obtained plate was determined using DNA assay. 100 µL of an SDS solution (20 mg of SDS was dissolved in 100 mL of a 1×SSC solution; the 1×SSC solution refers to a solution obtained by dissolving 17.999 g of NaCl and 8.823 g $Na_3$ Citrate in 2 L of ultrapure water) was added to each well of the obtained plate and left standing at 37° C. for 1 hour. The whole amount of each obtained solution was transferred to a 96-well black plate (Non-treated), and 100 µL of a Hoechst solution (prepared by mixing 20 µL of Hoechst 33258 with 20 mL of a 1×SSC solution) was added to each well. The fluorescence intensity was measured using a plate reader. The plate reader used was Gemini EM (Molecular Devices, LLC.), and the fluorescence intensity was measured at an excitation wavelength of 355 nm and a measurement wavelength of 460 nm. A calibration curve was prepared using a HUVEC cell suspension with the number of cells adjusted.

The obtained results of the cell adhesiveness test (DNA assay) are shown in FIGS. 17 and 18. Also, the manner of cell adhesion to the recombinant gelatin-coated plate is shown as a photograph in FIG. 19. These results showed that the recombinant gelatin had favorable cell adhesiveness.

Example 11

Preparation of Recombinant Gelatin Powder

A powder (particle shape) was prepared using the recombinant gelatin CBE3. In this Example, 7.5% CBE3 was used in the preparation. A solution is prepared according to composition shown below. After addition of glutaraldehyde, the mixture is sufficiently stirred at 25° C. and then directly subjected to cross-linking reaction at 4° C. for 16 hours.
Composition:
10 mL of 7.5% sponge (CBE3: 750 mg, ultrapure water: 8893.6 µL, 1 N HCl: 106.4 µL, 3% glutaraldehyde: 1000 µL).

A product obtained by standing/reaction at 4° C. for 16 hours is shaken for 4 hours in a sufficient amount of a 0.2 M glycine solution of 37° C. Then, washing with 10 L of ultrapure water is repeated 8 times (a total of 4 hours), and the resulting product is frozen at −80° C. for 2 hours. Then, freeze drying was performed for 4 days in a freeze drier, and the obtained dried product was pulverized with New Power Mill (Osaka Chemical Co., Ltd., New Power Mill PM-2005). The obtained pulverized products were sized through a stainless sieve to obtain a powder (particle shape) having a particle size of 500 to 710 µm.

Example 12

Bone Regeneration Evaluation in Rat Cranial Defect Model

A rat cranial defect model was used as a model in an animal experiment to evaluate the ability to regenerate bone (Tissue Eng (2007) 13 (3): 501-12). The rat cranial defect model is generally used in the evaluation of bone prosthetic materials.

Figure 20:
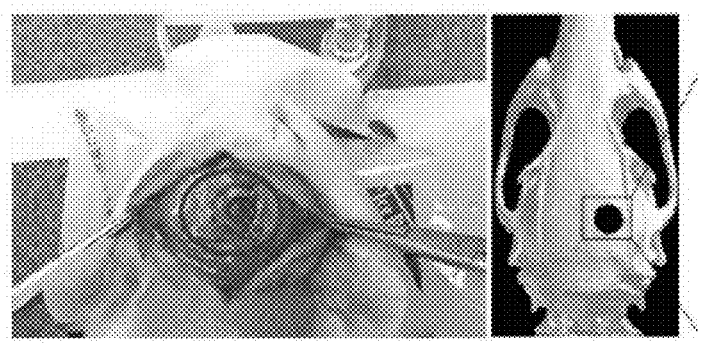
FIG. 20 shows a rat cranial defect model. Left: macroscopic photograph. Right: μCT photograph (Micro-CT image: Tissue Eng (2007) 13 (3): 501-12).

Sprague-Dawley rats (SD rats, male, 10-12 weeks old) were anesthetized, and a round defect (φ=5 mm) was prepared in the right parietal bone (FIG. 20) using a drill (Osada Success 40, Osada Electric Co., Ltd.). Bone chips or blood influencing bone regeneration were washed off from the defect with saline. A sample for bone regeneration evaluation was implanted into the prepared defect and covered with a collagen film (BioGide) to prevent the transplanted sample from flying out of the defect. Then, the skin of the affected part was sutured. After the predetermined period (2 weeks), each rat was sacrificed by opening of its abdomen and blood letting, and the affected part that was defected was macroscopically observed. Then, the head was fixed in formalin, decalcified, and embedded in paraffin. The paraffin-embedded block was sliced, and the obtained slice was stained with hematoxylin-eosin (H&E) to prepare a sample. For the evaluation, the pathological sample was observed with an optical microscope, and tissues were divided into New Bone, Mesenchyme, and Granulation based on taken photographs. Their respective areas were calculated. The ratio of regenerated bone (New Bone) in the defect and the amount ($\mu m^2$) of regenerated bone in the sample were evaluated.

Example 13

Evaluation of Bone Regeneration Rate of Recombinant Gelatin Sponge in Rat Cranial Defect The recombinant gelatin sponge (5%) prepared in Example 4 and the recombinant gelatin powder (particulate) prepared in Example 11 were separately transplanted to the rat cranial defect prepared in Example 12. A film made of collagen (BioGide, Osteohealth Company) was placed thereon to prevent the transplant from flying out thereof. Moreover, a group in which nothing was applied to the affected part was used as a control group.

As a result, for the recombinant gelatin powder (particulate)-transplanted group, the amount of bone regenerated was 209928 $\mu m^2$, and the ratio of regenerated bone was 6.8%. By contrast, for the recombinant gelatin sponge-transplanted group, the amount of bone regenerated was 732104 $\mu m^2$, and the ratio of regenerated bone was as high as 50.0%, showing that bone regeneration was induced exceedingly rapidly. This demonstrated that bone regenerating effect was significantly enhanced by imparting the structure of the present invention even if the same material was used.

Figure 21:
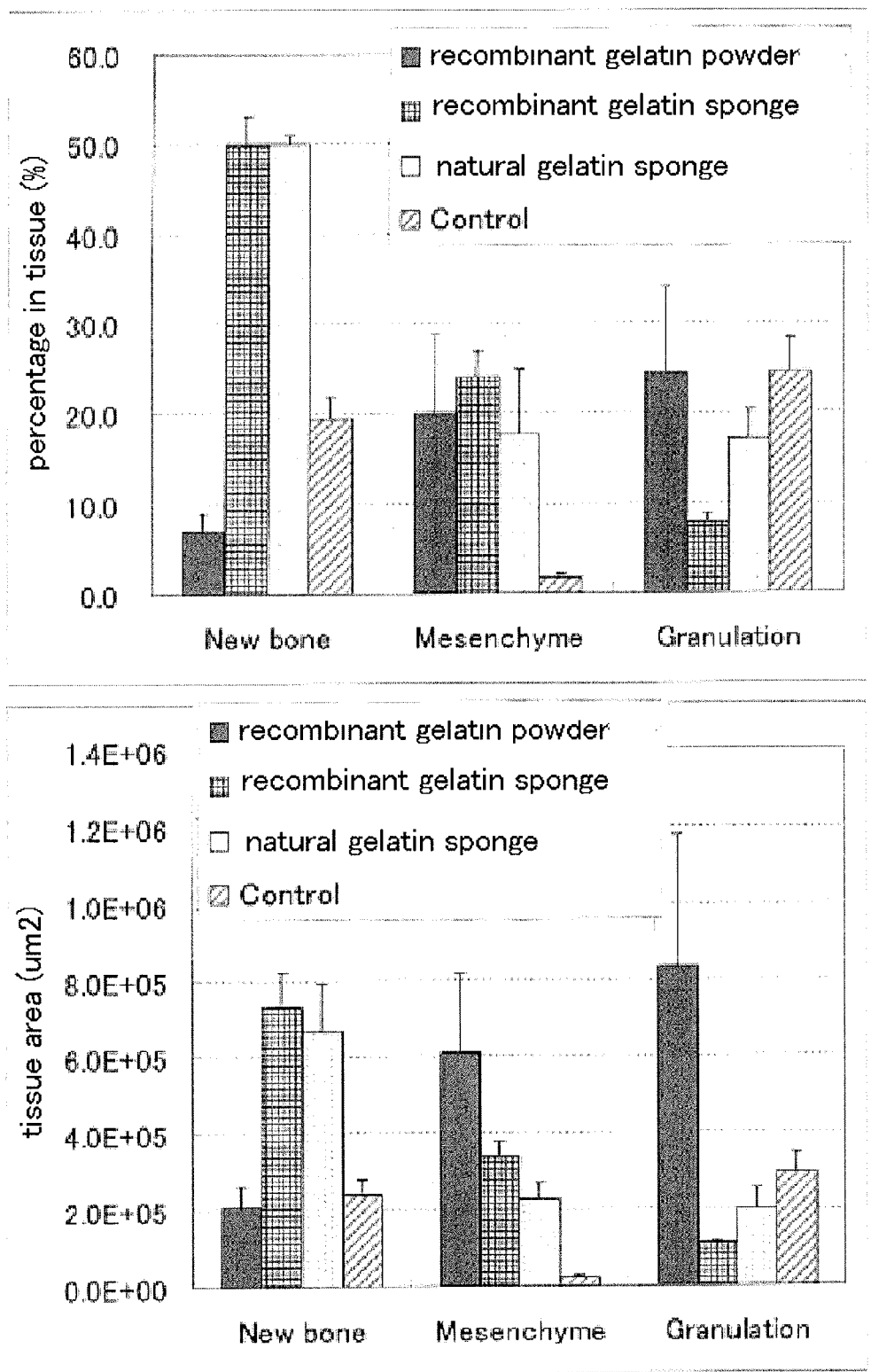
FIG. 21 shows data on the amount of bone regenerated and a bone regeneration rate.
Figure 22:
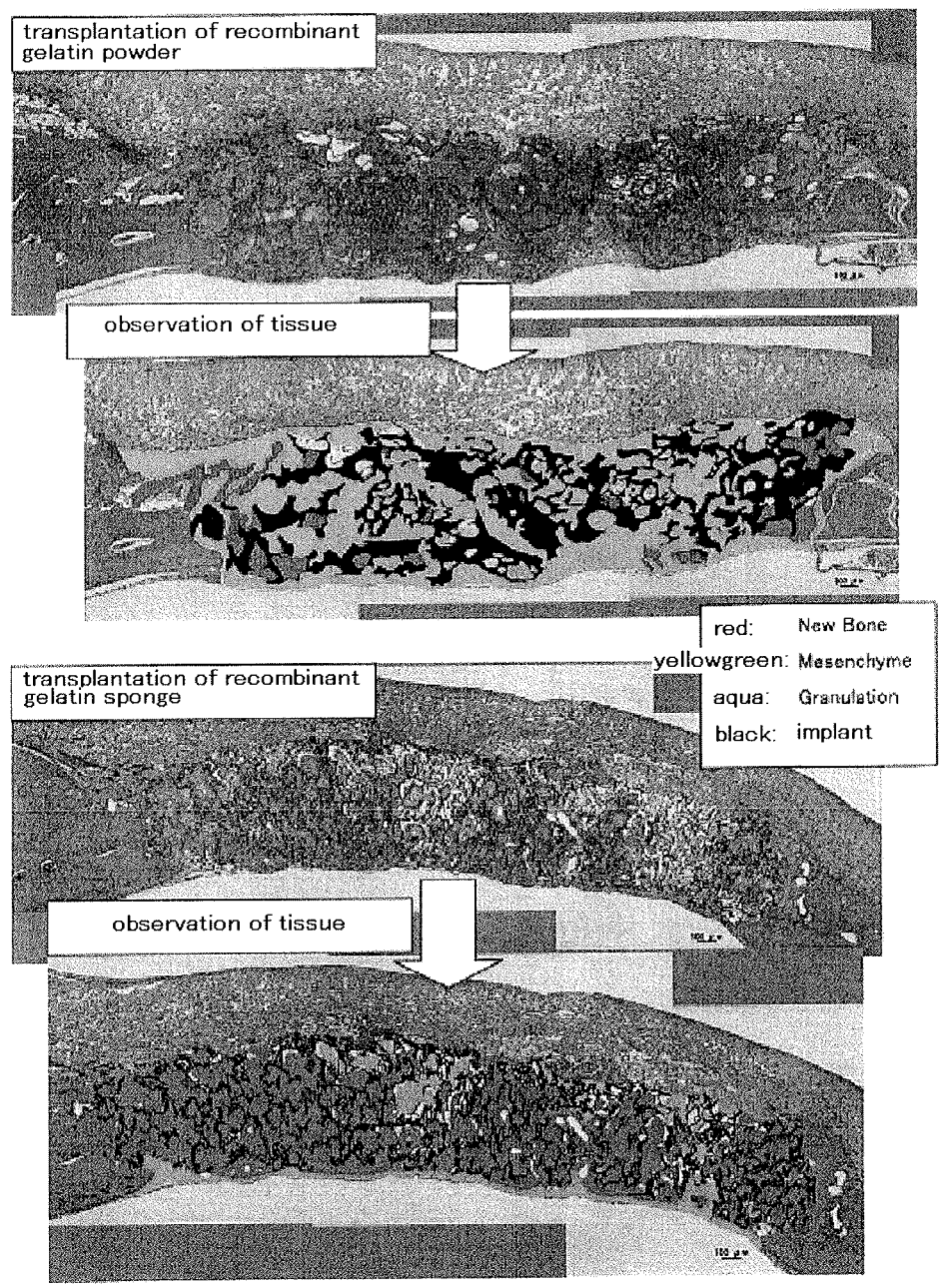
FIG. 22 shows typical pathological photographs of recombinant gelatin powder-transplanted and recombinant gelatin sponge-transplanted groups.

Data on the amount of bone regenerated and the bone regeneration rate was summarized in the table of FIG. 21. Also, typical pathological photographs of the recombinant gelatin powder-transplanted group and the recombinant gelatin sponge-transplanted group are shown in FIG. 22.

Example 14

Preparation of Natural Gelatin Sponge (Porous Body)

A natural gelatin sponge (porous body) was prepared using animal-derived natural gelatin APAT (Nippi, Nippi gelatin/high grade gelatin APAT). In this Example, 5% concentration was used in the preparation. A solution is prepared according to composition shown below. After addition of glutaraldehyde, the mixture is stirred at 17,000 rpm at 4° C. for 4 minutes using a homogenizer (AM-11, manufactured by Nippon Seiki Co., Ltd.) and directly cooled rapidly at −80° C. for 3 hours.
Composition:
10 mL of 5% sponge (APAT: 500 mg, ultrapure water: 9424 µL, 1 N HCl: 76 µL, 3% glutaraldehyde: 500 µL).

Then, a product obtained by standing at 4° C. for 16 hours is shaken for 4 hours in a sufficient amount of a 0.2 M glycine solution of 37° C. Then, washing with 10 L of ultrapure water is repeated 8 times (a total of 4 hours), and the resulting product is frozen at −80° C. for 2 hours. Then, freeze drying was performed for 4 days in a freeze drier to obtain a natural gelatin sponge (porous body).

Example 15

Evaluation of Bone Regeneration Rate of Natural Gelatin Sponge in Rat Cranial Defect The natural gelatin sponge (5%) prepared in Example 14 was transplanted to the rat cranial defect prepared in Example 12. A film made of collagen (BioGide, Osteohealth Company) was placed thereon to prevent the transplant from flying out thereof. Moreover, a group in which nothing was applied to the affected part was used as a control group.

Figure 23:
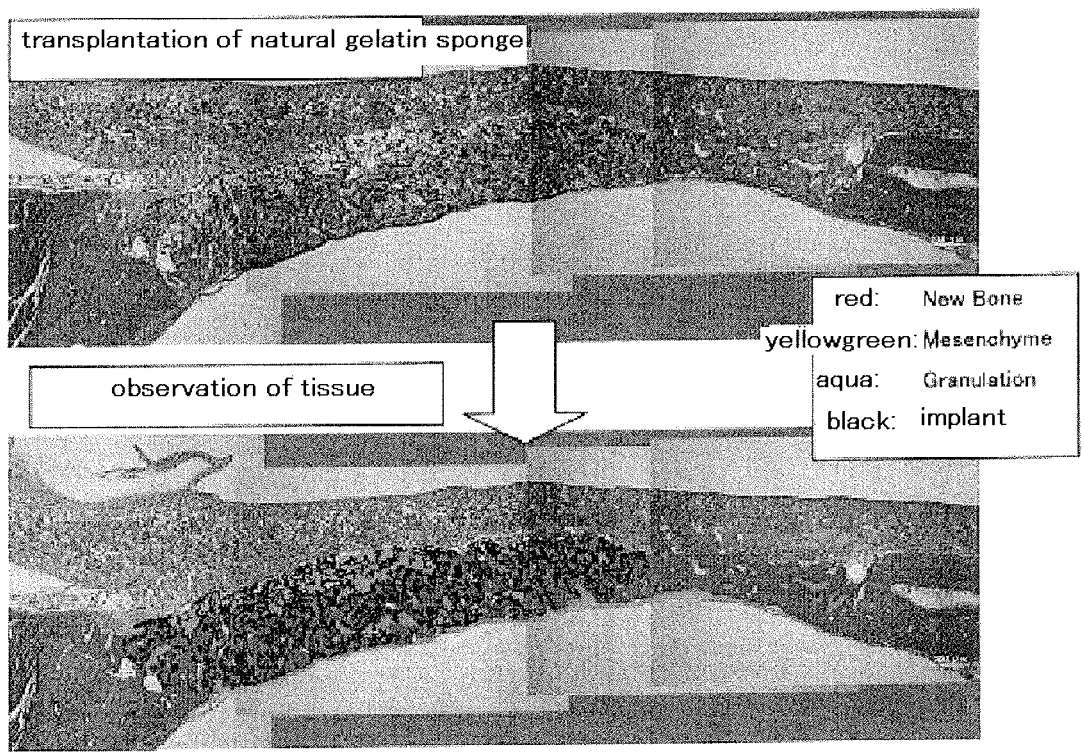
FIG. 23 shows a typical pathological photograph of a natural gelatin sponge-transplanted group.

As a result, for the natural gelatin sponge-transplanted group, the amount of bone regenerated was 819,960 μm$^2$, and the ratio of regenerated bone was as high as 59.0%, showing that bone regeneration was induced exceedingly rapidly. This demonstrated that the bone regenerating effect of even natural gelatin, which is a material that has generally been considered not suitable for bone regeneration so far, could be significantly enhanced by imparting thereto the structure of the present invention. Data on the amount of bone regenerated and the bone regeneration rate was summarized in the table of FIG. 21. Also, a typical pathological photograph of the natural gelatin sponge-transplanted group is shown in FIG. 23.

The invention claimed is:

1. A cell support consisting of a porous body made of a biodegradable material, the porous body having the following properties:
   (a) a porosity from 81% to 99.99%,
   (b) an average pore size of 10 to 400 μm,
   (c) having a hole interconnecting pores, and
   (d) a water absorption rate from 1000% to 9900%,
   wherein the porous body is obtained by freezing and freeze-drying an aqueous solution which contains the biodegradable material.

2. The cell support according to claim 1, wherein the biodegradable material has a Grand average of hydropathicity (GRAVY) value from −5.0 to 0.3.

3. The cell support according to claim 1, wherein the biodegradable material is at least one or more materials selected from protein, polypeptide, polylactic acid, polyglycolic acid, PLGA, chitin, chitosan, cellulose, and hyaluronic acid.

4. The cell support according to claim 1, wherein the biodegradable material is natural or recombinant gelatin, natural or recombinant fibronectin, or natural or recombinant laminin.

5. The cell support according to claim 1, wherein the biodegradable material is cross-linked.

6. The cell support according to claim 1, wherein the biodegradable material is recombinant gelatin.

7. The cell support according to claim 6, wherein the recombinant gelatin is represented by the formula:

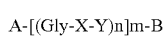

A-[(Gly-X-Y)n]m-B wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X-Y of total n may be the same as or different from each other.

8. The cell support according to claim 6, wherein the recombinant gelatin has any of the followings:
(1) the amino acid sequence represented by SEQ ID NO: 1, or
(2) an amino acid sequence having 80% or higher homology to the amino acid sequence represented by SEQ ID NO: 1 and having biodegradability.

9. A regenerative medicine material comprising a cell support according to claim 1.

10. A regenerative medicine material comprising a cell support according to claim 1 and a cell graft.

11. A bone regeneration material consisting of a porous body made of a biodegradable material, the porous body having the following properties:
(a) a porosity from 81% to 99.99%,
(b) an average pore size of 10 to 400 μm,
(c) having a hole interconnecting pores, and
(d) a water absorption rate from 1000% to 9900%,
wherein the porous body is obtained by freezing and freeze-drying an aqueous solution which contains the biodegradable material.

12. The bone regeneration material according to claim 11, wherein the biodegradable material has a Grand average of hydropathicity (GRAVY) value from −5.0 to 0.3.

13. The bone regeneration material according to claim 11, wherein the biodegradable material is at least one or more materials selected from protein, polypeptide, polylactic acid, polyglycolic acid, PLGA, chitin, chitosan, cellulose, and hyaluronic acid.

14. The bone regeneration material according to claim 11, wherein the biodegradable material is natural or recombinant gelatin, natural or recombinant fibronectin, or natural or recombinant laminin.

15. The bone regeneration material according to claim 11, wherein the biodegradable material is cross-linked.

16. The bone regeneration material according to claim 11, wherein the biodegradable material is recombinant gelatin.

17. The bone regeneration material according to claim 16, wherein the recombinant gelatin is represented by the formula:

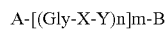

A-[(Gly-X-Y)n]m-B wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X-Y of total n may be the same as or different from each other.

18. The bone regeneration material according to claim 16, wherein the recombinant gelatin has any of the followings:
(1) the amino acid sequence represented by SEQ ID NO: 1, or
(2) an amino acid sequence having 80% or higher homology to the amino acid sequence represented by SEQ ID NO: 1 and having biodegradability.

19. A regenerative medicine material comprising a bone regeneration material according to claim 11.

20. A regenerative medicine material comprising a bone regeneration material according to claim 11 and a cell graft.

* * * * *

SEQUENCE LISTING

```
<160> NUMBER OF SEQ ID NOS: 1

<210> SEQ ID NO 1
<211> LENGTH: 571
<212> TYPE: PRT
<213> ORGANISM: Artificial Sequence
<220> FEATURE:
<223> OTHER INFORMATION: Synthtic peptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
                100                 105                 110

Asp Ala Gly Pro Lys Gly Ala Asp Gly Ala Pro Gly Lys Asp Gly Val
            115                 120                 125

Arg Gly Leu Ala Gly Pro Ile Gly Pro Pro Gly Pro Ala Gly Ala Pro
        130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
```

-continued

```
                 260                 265                 270
Asp Gly Val Arg Gly Leu Ala Gly Pro Ile Gly Pro Pro Gly Glu Arg
            275                 280                 285
Gly Ala Ala Gly Leu Pro Gly Pro Lys Gly Glu Arg Gly Asp Ala Gly
            290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
            340                 345                 350
Pro Lys Gly Glu Arg Gly Asp Ala Gly Pro Lys Gly Ala Asp Gly Ala
            355                 360                 365
Pro Gly Lys Asp Gly Val Arg Gly Leu Ala Gly Pro Pro Gly Ala Pro
            370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
                420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
            450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
                500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
            530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570
```